United States Patent
Wiles et al.

(10) Patent No.: US 12,156,517 B1
(45) Date of Patent: Dec. 3, 2024

(54) HUMANIZED MOUSE MODELS OF THE FcRn RECYCLING PATHWAY

(71) Applicant: The Jackson Laboratory, Bar Harbor, ME (US)

(72) Inventors: Michael V. Wiles, Bar Harbor, ME (US); Derry C. Roopenian, Bar Harbor, ME (US); Greg Christianson, Bar Harbor, ME (US); Benjamin E. Low, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 54 days.

(21) Appl. No.: 17/680,379

(22) Filed: Feb. 25, 2022

Related U.S. Application Data

(60) Provisional application No. 63/154,500, filed on Feb. 26, 2021.

(51) Int. Cl.
| | | |
|---|---|---|
| *A01K 67/027* | (2024.01) | |
| *A01K 67/0278* | (2024.01) | |
| *C07K 14/735* | (2006.01) | |
| *C07K 16/00* | (2006.01) | |
| *C07K 16/28* | (2006.01) | |
| *C07K 16/46* | (2006.01) | |

(52) U.S. Cl.
CPC .... *A01K 67/0278* (2013.01); *C07K 14/70535* (2013.01); *C07K 16/283* (2013.01); *A01K 2207/15* (2013.01); *A01K 2227/105* (2013.01); *C07K 2317/21* (2013.01); *C07K 2317/24* (2013.01); *C07K 2317/52* (2013.01); *C07K 2317/72* (2013.01); *C07K 2317/92* (2013.01); *C07K 2317/94* (2013.01)

(58) Field of Classification Search
CPC ............ A01K 67/0278; A01K 2207/15; C07K 14/70535; C07K 16/283
See application file for complete search history.

(56) References Cited

U.S. PATENT DOCUMENTS

| | | |
|---|---|---|
| 6,992,234 B2 | 1/2006 | Roopenian |
| 7,358,416 B2 | 4/2008 | Roopenian |
| 7,968,316 B2 * | 6/2011 | Jung .................. A61K 47/6811 435/69.6 |
| 8,771,960 B2 * | 7/2014 | Breitling ................ C07K 16/40 435/7.1 |
| 10,457,719 B2 | 10/2019 | Roopenian et al. |

OTHER PUBLICATIONS

Larijani et al. Molecular Immunology. 2006; 43: 870-881. (Year: 2006).*
Rudikoff et al. Proceedings of the National Academy of Sciences USA. 1982; 79: p. 1979-1983. (Year: 1982).*
McLean et al. Molecular Immunology. 2000; 37: 837-845. (Year: 2000).*
Betts et al., Linear pharmacokinetic parameters for monoclonal antibodies are similar within a species and across different pharmacological targets: A comparison between human, cynomolgus monkey and hFcRn Tg32 transgenic mouse using a population-modeling approach. MAbs. Jul. 2018;10(5):751-764. doi: 10.1080/19420862.2018.1462429. Epub May 14, 2018.
Fan et al., Tissue expression profile of human neonatal Fc receptor (FcRn) in Tg32 transgenic mice. MAbs. Jul. 2016;8(5):848-53. doi: 10.1080/19420862.2016.1178436. Epub Apr. 22, 2016.
Lee et al., An engineered human Fc domain that behaves like a pH-toggle switch for ultra-long circulation persistence. Nat Commun. Nov. 6, 2019;10(1):5031. doi: 10.1038/s41467-019-13108-2.
Low et al., Functional humanization of immunoglobulin heavy constant gamma 1 Fc domain human FCGRT transgenic mice. MAbs. Jan.-Dec. 2020;12(1):1829334. doi: 10.1080/19420862.2020.1829334.
Roopenian et al., FcRn: the neonatal Fc receptor comes of age. Nat Rev Immunol. Sep. 2007;7(9):715-25. doi: 10.1038/nri2155. Epub Aug. 17, 2007.
Stewart et al., The role of Fc gamma receptors in the activity of immunomodulatory antibodies for cancer. J Immunotherapy Cancer. 2014; 2(29): 1-10. Doi: 10.1186/s40425-014-0029-x.
Valente et al., Pharmacokinetics of novel Fc-engineered monoclonal and multispecific antibodies in cynomolgus monkeys and humanized FcRn transgenic mouse models. MAbs. Jan.-Dec. 2020;12(1):1829337. doi: 10.1080/19420862.2020.1829337.

\* cited by examiner

*Primary Examiner* — Taeyoon Kim
*Assistant Examiner* — Jianjian Zhu
(74) *Attorney, Agent, or Firm* — Wolf, Greenfield & Sacks, P.C.

(57) ABSTRACT

The present disclosure provides improved humanized IgG1 FCRN mouse models for use, for example, in estimating serum half-life of therapeutic proteins such as monoclonal antibodies.

5 Claims, 4 Drawing Sheets

Specification includes a Sequence Listing.

```
                       SEQUENCE LISTING

<160> NUMBER OF SEQ ID NOS: 7

<210> SEQ ID NO 1
<211> LENGTH: 4873
<212> TYPE: DNA
<213> ORGANISM: Artificial Sequence
<220> FEATURE:
<223> OTHER INFORMATION: Synthetic

<400> SEQUENCE: 1
aacaagaaca ggggaaatcc tagggctgac attgccagtg aaacataca  ggctggagct      60 ctttagtcag gagctccagc tgtgatctag acatcaggca ggaagatcaa atctgtccca     120
acaatacagg ggacagaggc tcaacctaga gtgtgagcat caggggctgt gcaggagatt     180
tcagagctca ggtgcagcag agactagcat ggccctgggg ataaagggaa ggatccaagg     240
gacaagggga taatcctggg gaggtaaggg ccagcttcgt gacagaaggt ggtggtgtcc     300
aacttcaaga gccctgtgct acaatttaaa aaaaaaaaaa aaggaaaggg acttctctgt     360
gtttggcaac acaagtgcga tgcacaggca ggaagatcaa atctgtccca acaatacagg     420
ggacagaggc tcaacctaca aaaggaaaga acctgggca gtgtgaagac aacactgtag     480
aagccaaggc tgagttcact gagctctcgt tagtgagact acacagcaag gaggtggcgg     540
gcactgagca gtgaggcccc gggaagtggg ggtgatggtg gtgacggtgg taactgttaa     600
gaactggggg aaagaattgt ggagaaccaa gctaaatagt tatgtcaaac cacatgttta     660
ggagcctggg ttgacttcat agggagtagg catgaggct aatctagagg tttgtgtata     720
ggcaagaagt gaatcctgac ccaagaatag agagtgctaa acggacttag ttcaaagaca     780
```

```
actgaaaaag acaatgcctg caaaacaaag ctaaggccag agctcttgga ctatgaagag      840
ttcagggaac ctaagaacag ggaccatctg tgtacaggcc aaggccggta gaagcagcct      900
aggaagtgtc aagagccaac gtggctgggt gggcaaagac aggaagggac tgttaggctg      960
cagggatgtg ccgacttcaa tgtgcttcag tattgtccag attgtgtgca gccatatggc     1020
ccaggtataa gaggtttaac agtggaacac agatgcccac atcagacagc tgggggggcgg    1080 gggtgaacac agatacccat actggaaagc aggtggggca ttttcctagg aacgggactg     1140
ggctcaatgg cctcaggtct catctggtct ggtgatcctg acattgatag gcccaaatgt     1200
tggatatcac ctactccatg tagagagtcg ggacatggg aagggtgcaa aagagcggcc      1260
ttctagaagg tttggtcctg tcctgtcctg tctgacagtg taatcacata actttttct      1320 tgtagccaaa acgacacccc catctgtcta tccactggcc cctggatctg ctgcccaaac    1380
taactccatg gtgaccctgg gatgcctggt caagggctat ttccctgagc cagtgacagt    1440
gacctggaac tctggatccc tgtccagcgg tgtgcacacc ttcccagctg tcctgcagtc    1500
tgacctctac actctgagca gctcagtgac tgtcccctcc agcacctggc ccagccagac    1560
cgtcacctgc aacgttgccc acccggccag cagcaccaag gtggacaaga aaattggtga    1620
gaggacgtat agggaggagg ggttcactag aggtgaggct caagccatta gcctgcctaa    1680
accaaccagg ctggacagcc atcaccagga aatggatctc agcccagaag atcgaaagtt    1740
gttcttctcc cttctggaga tttctatgtc ctttacactc attggttaat atcctgggtt    1800
ggattcccac acatcttgac aaacagagac aattgagtat caccagccaa aagtcatacc    1860
caaaaacagc ctggcatgac ctcacaccag actcaaactt accctacctt tatcctggtg    1920
gcttctcatc tccagacccc agtaacacat agctttctct ccacagtgcc caaatcttgt    1980
gacaaaactc acacatgccc accgtgccca ggtaagccag cccaggcctc gccctccagc    2040
tcaaggcggg acaggtgccc tagagtagcc tgcatccagg acaggccccc agccgggtgc    2100
tgacacgtcc acctccatct cttcctcagc acctgaactc ctggggggac cgtcagtctt    2160
cctcttcccc ccaaaaccca aggacaccct catgatctcc cggacccctg aggtcacatg    2220
cgtggtggtg gacgtgagcc acgaagaccc tgaggtcaag ttcaactggt acgtggacgg    2280
cgtggaggtg cataatgcca agacaaagcc gcgggaggag cagtacaaca gcacgtaccg    2340
tgtggtcagc gtcctcaccg tcctgcacca ggactggctg aatggcaagg agtacaagtg    2400
caaggtctcc aacaaagccc tcccagcccc catcgagaaa accatctcca aagccaaagg    2460
tgggacccgt ggggtgcgag ggccacatgg acagaggccg gctcggccca ccctctgccc    2520
tgagagtgac cgctgtacca acctctgtcc ctacagggca gccccgagaa ccacaggtgt    2580
acaccctgcc cccatcccgg gatgagctga ccaagaacca ggtcagcctg acctgcctgg    2640
tcaaaggctt ctatcccagc gacatcgccg tggagtggga gagcaatggg cagccggaga    2700
acaactacaa gaccacgcct cccgtgctgg actccgacgg ctccttcttc ctctacagca    2760
agctcaccgt ggacaagagc aggtggcagc aggggaacgt cttctcatgc tccgtgatgc    2820
atgaggctct gcacaaccac tacacacaga agagcctctc cctgtctcct ggtaaatgat    2880
cccagtgtcc ttggagccct ctggtcctac aggactctga cacctacctc cacccctccc    2940
tgtgtaaata aagcacccag cactgccttg ggaccctgca ataatgtcct ggtgatttct    3000
gagatgtaga gtctagctag gtcatggaat gaggggtctc catggtttga ggcctgagtt    3060
gtgactaagg aaaaacccat aggcctacac tgccacaccc agcacttttg aatttgcctg    3120
```

```
acatgaaaag aatttacctc tccctggaaa gtggagcctt atccctaggc agttccctta    3180
ccagaccttc ctctagcttg cactttgttc tgggcacaga atgtgtctaa cccccccaaag   3240
caaggaagac acaacctcta cctccctcac tctgtcctta ccccttttcc tggctaagca    3300
tctcactgag tgcgctgaat agatgcatgt ggccacagtc ttgcagacag acccttgcca    3360
tctctccact cagctttcca gaggctaagt ctagcccgta tggtgataat gcagggagct    3420
ctatgctatc tcagtgctat cagactccca agtggaggat gaacatggac ccattaaaac    3480
caacctgcgc agcaacaccc tgccaataag gcccgtatgt gaaaatgtgc acacatctac    3540
acatgcacag gcacacacac acacacatgc atgggcacac acacatacag agagagagaa    3600
tcacagaaac tcccatgagc atcctataca gtactcaaag ataaaaaggt accaggtcta    3660
cccacatgat catcctcggc atttacaagt gggccaactg atacagataa aacttttcta    3720
tgccaaggac gccaacatat acacaagtcc gctcatgaca aatctgtccc tgaacctcag    3780
actggcgccc gtgactcata cagtggacac tcctccaaag ctgtatagct tcctttactt    3840
ccctgtgtgt actttctctg aagtacactc atcacacaga gaggccctg  tgattactct    3900
ggccctctgt tcttggtcat cagagaatag acagaagatc aggcaaacta cacagacact    3960
tcccacaatc atcacaggcc ctgactctgc tctccagtct caaaactgaa ggctggagca    4020
cacagaataa gctcctgcac aggccaggcc agtatcgggt ccagtgtgtc tgactgagcc    4080
cagggacaaa atggcagcac tttggggaac tgaggtttct ggtccaagaa ggagagatgg    4140
aggcccaggg agggtctgct gacccagccc agcccagccc agctgcagct ttctcctggg    4200
cctccataca gcctcctgcc acacaggaa  tggccctagc cccaccttat tgggacaaac    4260
actgaccgcc ctctctgtcc agggctgcaa ctggacgaga cctgtgctga ggcccaggac    4320
ggggagctgg acgggctctg gacgaccatc accatcttca tcagcctctt cctgctcagt    4380
gtgtgctaca gcgctgctgt cacactcttc aaggtcagcc atactgtccc cacagtgtct    4440
acaatgtcct catactcttc cccatactgt ccctgtggtg acctatacc  cacactgtcc    4500
catgctaatg accacagtct tacatgctat gtaatgctgt ctacccttct gtatgcacag    4560
tctcacaatg tccatgcag  tctccacgat gctccatact gtccccattc caacccatgc    4620
tgccccttgt tccccgctat gctgtcccat gctattgtct gtattttcat gctcttttca    4680
cactgtccct agtgtcacat tctgcccatg ttgtccacca cattgtcccc actctgtaca    4740
cagcctcaca ctgtacccctg ctacccgata atgttccctg ttgtcccccaa ctctctccct    4800
gcaccatttg tcaactgtcc cctgaattcc catgttgttc ccacactgtt agtgtgtaat    4860
gtgctctgtc cca                                                      4873
```

<210> SEQ ID NO 2
<211> LENGTH: 11
<212> TYPE: PRT
<213> ORGANISM: Homo sapiens

<400> SEQUENCE: 2

Pro Lys Ser Cys Asp Lys Thr His Thr Cys Pro
1               5                   10

<210> SEQ ID NO 3
<211> LENGTH: 220
<212> TYPE: PRT
<213> ORGANISM: Homo sapiens

<400> SEQUENCE: 3

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
210                 215                 220
```

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
gcacaatccc tgggcactgt gg                                           22

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gagcctctcc cactctcctg g                                            21

<210> SEQ ID NO 6
<211> LENGTH: 397
<212> TYPE: PRT
<213> ORGANISM: Artificial Sequence
<220> FEATURE:
<223> OTHER INFORMATION: Synthetic

<400> SEQUENCE: 6

```
Lys Thr Thr Pro Pro Ser Val Tyr Pro Leu Ala Pro Gly Ser Ala Ala
1               5                   10                  15
```

```
Gln Thr Asn Ser Met Val Thr Leu Gly Cys Leu Val Lys Gly Tyr Phe
             20                  25                  30

Pro Glu Pro Val Thr Val Thr Trp Asn Ser Gly Ser Leu Ser Ser Gly
         35                  40                  45

Val His Thr Phe Pro Ala Val Leu Gln Ser Asp Leu Tyr Thr Leu Ser
     50                  55                  60

Ser Ser Val Thr Val Pro Ser Ser Thr Trp Pro Ser Gln Thr Val Thr
 65                  70                  75                  80

Cys Asn Val Ala His Pro Ala Ser Ser Thr Lys Val Asp Lys Lys Ile
                 85                  90                  95

Val Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Leu Gln Leu Asp Glu Thr Cys Ala Glu
                325                 330                 335

Ala Gln Asp Gly Glu Leu Asp Gly Leu Trp Thr Thr Ile Thr Ile Phe
            340                 345                 350

Ile Ser Leu Phe Leu Leu Ser Val Cys Tyr Ser Ala Ala Val Thr Leu
        355                 360                 365

Phe Lys Val Lys Trp Ile Phe Ser Ser Val Val Glu Leu Lys Gln Thr
    370                 375                 380

Leu Val Pro Glu Tyr Lys Asn Met Ile Gly Gln Ala Pro
385                 390                 395
```

<210> SEQ ID NO 7
<211> LENGTH: 328
<212> TYPE: PRT
<213> ORGANISM: Artificial Sequence
<220> FEATURE:
<223> OTHER INFORMATION: Synthetic

<400> SEQUENCE: 7

```
Lys Thr Thr Pro Pro Ser Val Tyr Pro Leu Ala Pro Gly Ser Ala Ala
1               5                   10                  15

Gln Thr Asn Ser Met Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Pro Ser Ser Thr Trp Pro Ser Gln Thr Val Thr
65                  70                  75                  80

Cys Asn Val Ala His Pro Ala Ser Ser Thr Lys Val Asp Lys Lys Ile
                85                  90                  95

Val Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325
```

HUMANIZED MOUSE MODELS OF THE FcRn RECYCLING PATHWAY

RELATED APPLICATIONS

This application claims the benefit under 35 U.S.C. § 119(e) of U.S. provisional application No. 63/154,500, filed Feb. 26, 2021, which is incorporated by reference herein in its entirety.

GOVERNMENT LICENSE RIGHTS

This invention was made with government support under OD011190 awarded by National Institutes of Health. The government has certain rights in the invention.

SEQUENCE LISTING

The instant application contains a Sequence Listing which has been submitted electronically in ASCII format and is hereby incorporated by reference herein in its entirety. Said ASCII copy, created on Feb. 23, 2022, is named J022770080US01-SEQ-EMB.txt and is 15,655 bytes in size.

BACKGROUND

The use of therapeutic proteins such as monoclonal antibodies are among the fastest growing and most promising advances in modern healthcare, leading a revolution in many therapeutic areas, including cancer, inflammatory disease, and diabetes. An important step toward bringing novel therapeutic proteins to market is obtaining an accurate estimate of the elimination half-life of the proteins. The elimination half-life of a therapeutic protein is a pharmacokinetic parameter that is defined as the time it takes for the concentration of the protein in the blood (e.g., serum) to be reduced by 50%. The elimination half-life is a useful pharmacokinetic parameter as it provides an accurate indication of the length of time that the effect of the therapeutic protein persists in an individual. It can also show if accumulation of the protein is likely to occur with a multiple dosing regimen. This is helpful when it comes to deciding the appropriate dose amount and frequency.

The elimination half-life of therapeutic proteins in an individual is regulated by the recycling molecule neonatal Fc receptor (FcRn). FcRn binds to the protein intracellularly to initiate the recycling pathway through which the protein is diverted away from the lysosomal degradation pathway and is instead transported in recycling transport vesicles to the cell surface, where it is released back into the serum as reviewed in Roopenian, D. C., et al. Nat. Rev. Immunol, 2007; 7:715-725. The use of mouse models to replicate this pathway in human, to evaluate the in vivo stability of therapeutic antibodies and other Fc-based biologics for example, is an effective and proven alternative to the use of non-human primates (Valente, D., et al. MABS, 2020; 12(1): 1829337, and Betts, A., et al. MABS, 2018; 10(5):1462429).

SUMMARY

A major asset of many monoclonal antibody (mAb)-based biologics is their persistence in circulation. The MHC class I family Fc receptor, FCGRT, is primarily responsible for this extended pharmacokinetic behavior. Engagement of FCGRT with the crystallizable fragment (Fc) domain protects IgG from catabolic elimination, thereby extending the persistence and bioavailability of IgG and related Fc-based biologics. There is a need for reliable in vivo models to facilitate the preclinical development of novel IgG-based biologics. FcRn-humanized mice have been widely accepted as translationally relevant surrogates for IgG-based biologics evaluations. Although such FCGRT-humanized mice, especially the mouse strain, B6.Cg-Fcgrttm1Dcr Tg(FCGRT)32Dcr (abbreviated Tg32; JAX Stock #014565), have been substantially validated for modeling humanized IgG-based biologics, there is a recognized caveat—they lack an endogenous source of human IgG that typifies the human competitive condition. Herein, CRISPR/Cas9-mediated homology-directed repair was used to equip the hFCGRT Tg32 strain with a human IGHG1 Fc domain. This replacement now results in mice that produce human IgG1 Fc-mouse IgG Fab2 chimeric antibodies at physiologically relevant levels, which can be further heightened by immunization. This endogenous chimeric IgG1 significantly dampens the serum half-life of administered humanized mAbs in an hFCGRT-dependent manner. Thus, such IgG1-Fc humanized mice may provide a more physiologically relevant competitive hFCGRT-humanized mouse model for the preclinical development of human IgG-based biologics. See Low, B. E., et al. MABS, January-December 2020; 12(1): 1829334, which is incorporated by reference herein in its entirety.

The current Tg32 mouse model carries a knock-out mutation for the mouse Fcgrt (Fc receptor, IgG, alpha chain transporter) gene and a transgene expressing the human FCGRT gene under the control of its own native promoter (hTg32). This Tg32 mouse model, while useful in evaluating the pharmacokinetics and pharmacodynamics of human immunoglobulin G (IgG) and Fc-domain based therapeutics, lacks IgG that can compete for hFcRn-mediated antibody recycling, due to the species-discrimination of human FcRn and the resulting failure to recycle and maintain physiological levels of mouse IgG. The lack of competing human IgG in the Tg32 mouse model limits its use in preclinical modeling of antibody recycling. There is no competition between an exogenous test human IgG (e.g., mAb) and endogenous mouse IgG for the hFcRn recycling pathway. This limitation means that the Tg32 mouse model and similar mouse models currently available only partially reflect normal human physiologically of antibody turnover, confounding pharmacokinetic (PK) studies for novel monoclonal antibody-based therapeutics, for example.

To overcome this limitation the improved humanized FcRn mouse models provided herein are genetically modified to include chimeric IgG1 that includes a fully human Fc region (~0.9 kb region including the hinge, CH2 and CH3 domains) joined to a fully mouse Fab region with an intact mouse variable region. This chimeric IgG1, with its human IgG1 Fc region, can bind human FcRn (e.g., genomically encoded by a FCGRT transgene) to facilitate antibody recycling. Surprisingly, data provided herein shows that this mouse model, unlike other similar models, produces levels of serum IgG1, which rise following immunization with 2,4-Dinitrophenyl hapten conjugated to keyhole limpet hemocyanin (DNP-KLH). In particular, naïve Tg32-hFc mice yielded chimeric IgG1 levels that ranged from 280 to 1,320 µg/ml (mean 600 µg/ml) and following immunization of Tg32-hFc mice with 2,4-dinitrophenyl-keyhole limpet hemocyanin (DNP-KLH), chimeric IgG1 was significantly increased (mean value 4,200 µg/ml) (see FIG. 2a of Low, B. E., et al. MABS, January-December 2020; 12(1): 1829334). This is well above level observed with the current mouse models. Further, data provided herein following treatment with two different monoclonal antibodies (1) HuLys11, a humanized monoclonal antibody (mAb) containing the CH1-3 region of human IgG1 that was raised against hen egg-white lysozyme, and (2) trastuzumab, a humanized mAb that binds the extracellular domain of the HER2 receptor and is in clinical use, demonstrates the occurrence of competition for human FcRn-mediated antibody recycling, closely reflecting normal physiologically function in humans. See Low, B. E., et al. (2020).

There is another beneficial outcome resulting from immunizing Tg32 mice expressing chimeric IgG1 with DNP-KLH: the demonstration of the utility of this mouse model to produce affinity matured chimeric IgG1 monoclonal antibodies that could act as therapeutic candidates. While the mg/ml serum concentrations of chimeric IgG1 became elevated following immunization, a large portion of the chimeric IgG1 activity was also demonstrated to be DNP-specific (FIG. 4). While DNP-specificity was demonstrated, any human therapeutic target could easily have been substituted yielding a chimeric IgG1 target-specific outcome.

Thus, some aspects of the present disclosure provide a mouse comprising a nucleic acid encoding human neonatal Fc receptor (FCRN) and a nucleic acid encoding a chimeric immunoglobulin that comprises a human immunoglobulin gamma (IgG) Fc region and a mouse Fab region, wherein the mouse comprises a null mutation in endogenous FcRn.

In some embodiments, the human IgG Fc region is a human IgG1 Fc region.

In some embodiments, cells of the mouse express the human FCRN and the chimeric immunoglobulin (B6.Cg-Fcgrt$^{tm1Dcr}$ Ighg1$^{em2(IGHG1)Mvw}$ Tg(FCGRT)32Dcr/Mvw; also referred to as Tg32-hFc. JAX Stock #029686).

In some embodiments, a level of the chimeric immunoglobin in serum of the mouse is at least 280 µg/ml. For example, a level of the chimeric immunoglobin in serum of the naïve mouse may be 280 µg/ml to 1,320 µg/ml.

In some embodiments, the Fab region comprises a mouse constant light chain (mC$_L$) sequence and/or a mouse constant heavy chain 1 (mC$_{H1}$) sequence.

In some embodiments, the Fab region comprises a mouse variable light chain (mV$_L$) sequence and/or mouse variable heavy chain (mV$_H$) sequence.

In some embodiments, the human IgG1 Fc region comprises a human heavy chain 2 (hC$_{H2}$) sequence and/or a human heavy chain 3 (hC$_{H3}$) sequence.

In some embodiments, the human IgG1 Fc region comprises a human heavy chain sequence having at least 80%, at least 85%, at least 90%, at least 95%, or 100% identity to the amino acid sequence of SEQ ID NO: 3.

In some embodiments, the immunoglobulin comprises a human hinge sequence.

In some embodiments, the human hinge sequence comprises the amino acid sequence of SEQ ID NO: 2.

In some embodiments, the nucleic acid encoding the immunoglobulin comprises a sequence that has at least 70%, at least 75%, at least 80%, at least 85%, at least 90%, at least 95%, or 100% identity to the sequence of SEQ ID NO: 1.

In some embodiments, the human FcRn is encoded by human FCGRT (Fc receptor, IgG, alpha chain transporter).

In some embodiments, the chimeric immunoglobulin competes with exogenous IgG for binding to the human FcRn.

Also provided herein is a nucleic acid or set of nucleic acids encoding a chimeric immunoglobulin, wherein the chimeric immunoglobulin comprises a human immunoglobulin gamma (IgG) Fc region and a mouse Fab region.

Further provided herein is a chimeric immunoglobulin comprising a human IgG Fc region and a mouse Fab region.

Some aspects of the present disclosure provide a method of producing the mouse of any one of the preceding claims comprising modifying the genome of a mouse to express a nucleic acid or set of nucleic acids encoding a chimeric immunoglobulin, wherein the chimeric immunoglobulin comprises a human IgG Fc region and a mouse Fab region. In some embodiments, the mouse expresses human FCRN.

Other aspects of the present disclosure provide a method of producing a mouse comprising modifying the genome of a B6.Cg-Fcgrt$^{tm1Dcr}$Tg(FCGRT)32Dcr/DcrJ (Tg32) mouse to express a nucleic acid or set of nucleic acids encoding a chimeric immunoglobulin, wherein the chimeric immunoglobulin comprises a human IgG Fc region and a mouse Fab region.

Yet other aspects of the present disclosure provide a method comprising administering to the mouse a therapeutic antibody and assaying half-life of the therapeutic antibody in serum of the mouse. In some embodiments, the therapeutic antibody is a monoclonal IgG antibody. In some embodiments, the monoclonal IgG antibody is a monoclonal IgG1 antibody.

Still other aspects of the present disclosure provide a use of the mouse of any one of the preceding paragraphs to produce Fc-humanized IgG1 monoclonal antibodies.

DETAILED DESCRIPTION

Figure 1:
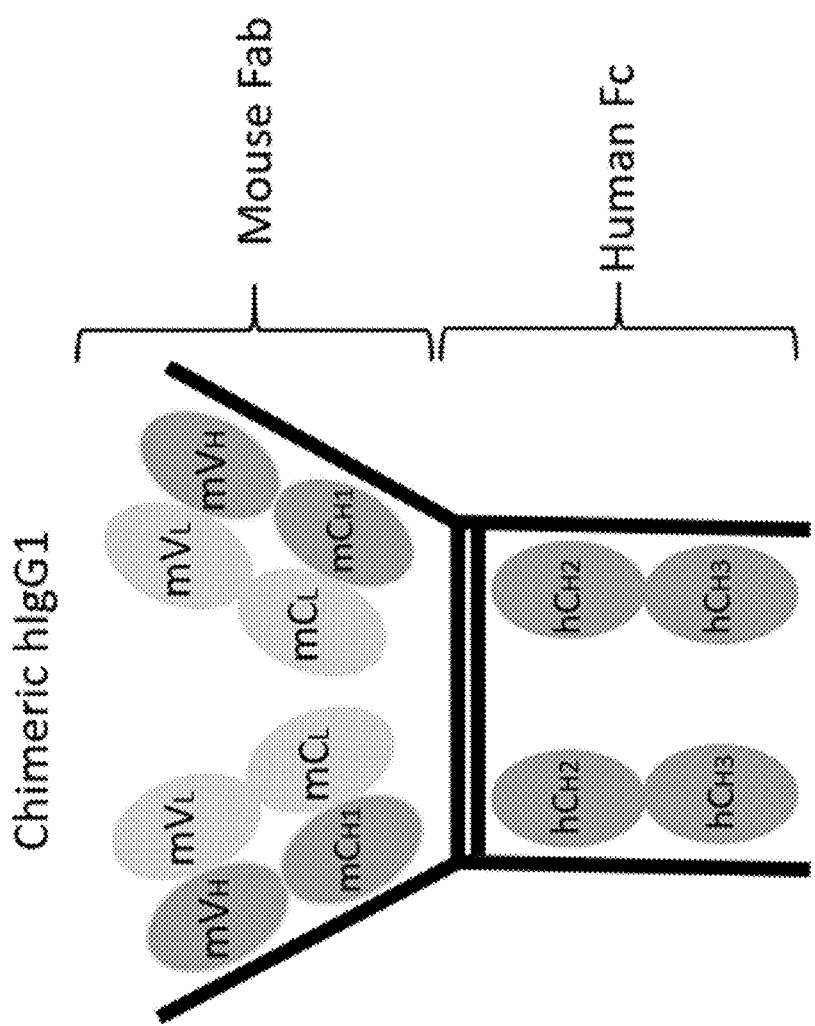
FIG. 1 shows the structure of a chimeric IgG1 antibody of the present disclosure having a fully mouse Fab region and a fully human Fc region. Each heavy chain portion of the Fab region includes a mouse variable heavy chain domain (mV$_H$) and a mouse constant heavy chain domain 1 (mC$_{H1}$), and each light chain portion of the Fab region includes a mouse variable light chain domain (mV$_L$) and a mouse constant light chain domain (mC$_L$). Each heavy chain portion of the Fc region includes a human constant heavy chain domain 2 (hC$_{H2}$) and a human constant heavy chain domain 3 (hC$_{H3}$). The hinge region is depicted as double solid lines.

The present disclosure provides, in some aspects, a mouse model that may be used to predict the half-life of candidate therapeutic antibodies (e.g., IgG antibodies) by modeling the recycling of human immunoglobulin gamma 1 (IgG1) antibodies. The neonatal Fc receptor (FcRn) rescues both albumin and IgG following endocytosis and thereby extends the half-life of these proteins. Exogenous IgG antibodies introduced into humans (and mice) compete with endogenous IgG1 for recycling, resulting in lower (e.g., shorter) serum half-lives of the antibodies. In order to accurately predict the half-life of a candidate therapeutic antibodies, for example, it is important that the mouse model genomically express physiologically-relevant levels of human FcRn and human or humanized IgG1. Mouse IgG1 cannot effectively compete with exogenous therapeutic antibodies for binding to human FcRn.

Thus, the development of the Tg32-hFc mice described herein provides a relevant and economic model to rapidly evaluate novel engineered Fc-based biologics within a more competitive environment, and could provide a more reliable preclinical PK analyses model. This Tg32-hFc model also provides a convenient vehicle for the rapid generation of Fc-humanized IgG1 monoclonal antibodies.

Thus, provided herein, in some aspects, are mouse models comprising a genomically-expressed chimeric immunoglobulin that competes with exogenous IgG for binding to human FcRn. Exemplary methods for assessing antibody competition for human FcRn-mediated IgG1 recycling is provided in Example 2.

Human Neonatal Fc Receptor (FcRn) and IgG

The mouse models provided herein, in some embodiments, comprise a nucleic acid encoding a human neonatal Fc receptor (FcRn). FcRn, encoded by the Fcgrt gene, is an MHC class I-like transmembrane protein that includes a heavy chain containing three extracellular domains ($\alpha 1$, $\alpha 2$ and $\alpha 3$), a single pass transmembrane domain and a short cytoplasmatic tail. For proper function, the FcRn heavy chain non-covalently associates with the common β2-microglobulin subunit as a light chain, which interacts with FcRn via residues on the underside of the $\alpha 1$-$\alpha 2$ platform and the side of the $\alpha 3$ domain. Intracellular binding of FcRn to an immunoglobulin such as IgG1 initiates the recycling pathway through which the IgG1 is diverted away from the lysosomal degradation pathway. The IgG is instead transported in recycling transport vesicles to the cell surface where it is released back into the serum.

The human FcRn expressed by cells of the mouse models provided herein, in some embodiments, is encoded by a transgene. In some embodiments, the transgene comprises the sequence of the human FCGRT gene (e.g., NCBI Gene ID: 2217). In some embodiments, the transgene comprises an hTg32 promoter.

The hFcRn, in some embodiments, is expressed in tissue of the mouse model at physiologically relevant levels.

The mouse models provided herein, in some embodiments, comprise a nucleic acid encoding a chimeric immunoglobulin, such as IgG. IgG molecules are approximately 150 kDa and composed of two identical light chains and heavy chains. IgG is the most abundant immunoglobulin in humans. It should be understood that "a nucleic acid encoding a chimeric immunoglobulin" encompasses a single nucleic acid or multiple nucleic acids encoding the heavy chains and light chains of the immunoglobulin.

A chimeric immunoglobulin is genetically engineered, for example, by joining the regions of a mouse immunoglobulin to regions of a human immunoglobulin. The chimeric IgG provided herein includes a human Fc region (e.g., including a hinge region, a $hC_{H2}$ domain, a $hC_{H3}$ domain) and a mouse Fab region (e.g., including a $mV_H$, $mV_L$, $mC_{H1}$, and $m_{CL}$). The fragment crystallizable (Fc) region is the tail region of an immunoglobulin that interacts with cell surface receptors referred to as Fc receptors and some proteins of the complement system to activate the immune system. The Fc region of IgG, for example, includes two identical protein fragments, derived from the second and third constant domains of the two heavy chains. The antigen-binding fragment (Fab) is a region on an immunoglobulin that binds to antigens. It includes a constant domain and a variable domain of each of the heavy and the light chain. The variable domain contains the paratope (the antigen-binding site), comprising a set of complementarity-determining regions, at the amino terminal end of the monomer. Each arm of the Y thus binds an epitope on the antigen.

In some embodiments, the human IgG1 Fc region comprises a human heavy chain sequence having at least 80% identity to the amino acid sequence of SEQ ID NO: 3. For example, the human IgG1 Fc region may comprise a human heavy chain sequence having at least 85%, at least 90%, at least 95%, or 100% identity to the amino acid sequence of SEQ ID NO: 3.

The hinge region of an immunoglobulin is a flexible amino acid stretch in the central part of the heavy chains of the immunoglobulin that links these two chains by disulfide bonds. In some embodiments, an immunoglobulin comprises a human hinge sequence. In some embodiments, the human hinge sequence comprises the amino acid sequence of SEQ ID NO: 2.

In some embodiments, the immunoglobulin comprises a heavy chain sequence that has at least 80%, at least 85%, at least 90%, at least 95%, or 100% identity to the amino acid sequence of SEQ ID NO: 6 or SEQ ID NO: 7.

In some embodiments, the nucleic acid encoding the immunoglobulin comprises a sequence that has at least 80%, at least 85%, at least 90%, at least 95%, or 100% identity to the amino acid sequence of SEQ ID NO: 1.

In some embodiments, a level of the chimeric immunoglobin in serum of the mouse is at least 280 µg/ml. For example, the chimeric immunoglobulin may be expressed at a level of 3.0 mg/ml, 3.5 mg/ml, 4.0 mg/ml, 4.5 mg/ml, 5.0 mg/ml, 5.5 mg/ml, 6.0 mg/ml, 6.5 mg/ml, 7.0 mg/ml, 7.5 mg/ml, 8.0 mg/ml, 8.5 mg/ml, 9.0 mg/ml, 9.5 mg/ml, 10.0 mg/ml, 10.5 mg/ml, 11.0 mg/ml, 11.5 mg/ml, or 12.0 mg/ml. In some embodiments, a level of the chimeric immunoglobin in serum of the mouse is 3.0 mg/ml to 12 mg/ml, 3.5 mg/ml to 12 mg/ml, 4.0 mg/ml to 12 mg/ml, 4.5 mg/ml to 12 mg/ml, 5.0 mg/ml to 12 mg/ml, 5.5 mg/ml to 12 mg/ml, 6.0 mg/ml to 12 mg/ml, 6.5 mg/ml to 12 mg/ml, 7.0 mg/ml to 12 mg/ml, 7.5 mg/ml to 12 mg/ml, 8.0 mg/ml to 12 mg/ml, 8.5 mg/ml to 12 mg/ml, 9.0 mg/ml to 12 mg/ml, 9.5 mg/ml to 12 mg/ml, 10.0 mg/ml to 12 mg/ml, or 10.5 mg/ml to 12 mg/ml.

Mouse Models

The mouse models of the present disclosure are based on the mouse model having the genotype B6.Cg-Fcgrt$^{tm1Dcr}$ Tg(FCGRT)32Dcr/DcrJ (also referred to Tg32, JAX Stock

014565). Tg32 mice carry a knock-out mutation for the mouse Fcgrt (Fc receptor, IgG, alpha chain transporter) gene and a transgene expressing the human FCGRT gene under the control of its own native promoter (hTg32). The genome of the Tg32 mouse model, however, encodes endogenous mouse IgG1 and thus these mice are limited with respect to their use in assessing the FcRn recycling pathway-mouse IgG1 cannot compete with exogenous immunoglobulins (e.g., IgG antibodies) for binding to FcRn.

The mouse models provided herein address this limitation by providing mice that instead express a chimeric form of IgG1(B6.Cg-Fcgrt$^{tm1Dcr}$ Ighg1$^{em2(IGHG1)Mvw}$ Tg(FCGRT) 32Dcr/Mvw; also referred to as Tg32-hFc, JAX Stock #029686), which is unexpectedly expressed at levels comparable to human IgG1 expression levels. These chimeric IgG1 expression levels are thus physiologically relevant and can be further heightened by immunization with antibodies (e.g., humanized monoclonal antibodies). Additionally, these chimeric IgG1 antibodies compete with exogenous immunoglobulins for binding to endogenous FcRn.

Herein, for simplicity, reference is made to "mouse" and "mouse models" (e.g., surrogates for human conditions). It should be understood that these terms, unless otherwise stated, may be used interchangeably throughout the specification to encompass "rodent" and "rodent models," including mouse, rat and other rodent species.

It should also be understood that standard genetic nomenclature used herein provides unique identification for different rodent strains, and the strain symbol conveys basic information about the type of strain or stock used and the genetic content of that strain. Rules for symbolizing strains and stocks have been promulgated by the International Committee on Standardized Genetic Nomenclature for Mice. The rules are available on-line from the Mouse Genome Database (MGD; informatics.jax.org) and were published in print copy (Lyon et al. 1996). Strain symbols typically include a Laboratory Registration Code (Lab Code). The registry is maintained at the Institute for Laboratory Animal Research (ILAR) at the National Academy of Sciences, Washington, D.C. Lab Codes may be obtained electronically at ILAR's web site (nas.edu/cls/ilarhome.nsf). See also Davisson MT, Genetic and Phenotypic Definition of Laboratory Mice and Rats/What Constitutes an Acceptable Genetic-Phenotypic Definition, National Research Council (US) International Committee of the Institute for Laboratory Animal Research. Washington (DC): National Academies Press (US); 1999.

The mouse models provide herein are transgenic mouse models that express human FCRN and a chimeric mouse/human IgG antibody, and do not express mouse FcRn. A transgenic mouse is a mouse having an exogenous nucleic acid (e.g., transgene) in (integrated into) its genome. Methods of producing transgenic mice are well-known.

Three conventional methods used for the production of transgenic mice include DNA microinjection (Gordon and Ruddle, *Science* 1981: 214: 1244-124, incorporated herein by reference), embryonic stem cell-mediated gene transfer (Gossler et al., *Proc. Natl. Acad. Sci.* 1986, 83: 9065-9069, incorporated herein by reference) and retrovirus-mediated gene transfer (Jaenisch, *Proc. Natl. Acad. Sci.* 1976, 73: 1260-1264, incorporated herein by reference), any of which may be used as provided herein. Genomic editing methods using, for example, clustered regularly interspace palindromic repeats (CRISPR/Cas) nucleases, transcription activator-like effector nucleases (TALENs), or zinc finger nucleases (ZFNs) are described elsewhere herein.

Following delivery of nucleic acids to a fertilized embryo (e.g., a single-cell embryo (e.g., a zygote) or a multi-cell embryo (e.g., a developmental stage following a zygote, such as a blastocyst), the fertilized embryo is transferred to a pseudopregnant female, which subsequently gives birth to offspring. The presence or absence of a nucleic acid encoding human FcRn and/or a chimeric IgG antibody may be confirmed, for example, using any number of genotyping methods (e.g., sequencing and/or genomic PCR).

Immunodeficient Mouse Models

Provided herein, in some embodiments, are immunodeficient mouse models. As is known in the art, immunodeficient mice have impaired or disrupted immune systems, such as specific deficiencies in MHC class I, II or both, B cell or T cell defects, or defects in both, as well as immunodeficiency due to knockdown of genes for cytokines, cytokine receptors, TLR receptors and a variety of transducers and transcription factors of signaling pathways. Immunodeficiency mouse models include the single-gene mutation models such as nude-mice (nu) strains and the severe combined immunodeficiency (scid) strains, non-obese diabetic (NOD) strain, RAG (recombination activating gene) strains with targeted gene deletion and a variety of hybrids originated by crossing doubly and triple mutation mice strains with additional defects in innate and adaptive immunity.

Non-limiting examples of spontaneous and transgenic immunodeficient mouse models include the following mouse strains:

Nude (nu) [Flanagan S P. *Genet Res* 1966; 8: 295-309; and Nehls M et al. *Nature* 1994; 372: 103-7];

Scid (scid) [Bosma G C et al. *Nature* 1983; 301:527-30; Mosier D E et al. *Nature* 1988; 335: 256-9; and Greiner D L et al. *Stem Cells* 1998; 16: 166-77];

NOD [Kikutani H et al. *Adv Immunol* 1992; 51: 285-322; and Anderson M S et al. *Ann Rev Immunol* 2005; 23: 447-85];

RAG1 and RAG2 (rag) [Mombaerts P et al. *Cell* 1992; 68: 869-77; Shinkai U et al. *Cell* 1992; 68: 855-67];

NOD-scid [Greiner D L et al. 1998; Shultz L D et al. *J Immunol* 1995; 154: 180-91; Melkus M W et al. *Nature Med* 2006; 12: 1316-22; and Denton P W et al. *PLOS Med* 2008; 4(12): e357];

IL2rgnull [DiSanto J P et al. *Proc Natl Acad Sci USA* 1995; 92: 377-81];

B2mnull [Christianson S W et al. *J Immunol* 1997; 158: 3578-86];

NOD-scid IL2rγnull [Shultz L D et al. *Nat Rev Immunol* 2007; 7: 118-30; Ito M et al. *Blood* 2002; 100: 3175-82; Ishikawa I et al. *Blood* 2005; 106: 1565-73; and Macchiarini F et al. *J Exp Med* 2005; 202: 1307-11];

NOD-scid B2mnull [Shultz et al. 2007; Shultz L D et al. *Transplantation* 2003; 76: 1036-42; Islas-Ohlmayer M A et al. *J Virol* 2004; 78:13891-900; and Macchiarini et al. 2005]; and HLA transgenic mice [Grusby M J et al. *Proc Natl Acad Sci USA* 1993; 90(9): 3913-7; and Roy C J et al. *Infect Immun* 2005; 73(4): 2452-60]. See, e.g., Belizario J E The Open Immunology Journal, 2009; 2:79-85.

Provided herein, in some embodiments, are immunodeficient mouse models having the non-obese diabetic (NOD) mouse genotype. The NOD mouse (e.g., Jackson Labs Stock #001976, NOD-Shi$^{LtJ}$) is a polygenic mouse model of autoimmune (e.g., Type 1) diabetes, characterized by hyperglycemia and insulitis, a leukocytic infiltration of the pancreatic islet cells. The NOD mice are hypoinsulinemic and hyperglucagonemic, indicating a selective destruction of pancreatic islet beta cells. The major component of diabetes susceptibility in NOD mice is the unique MHC haplotype. NOD mice also exhibit multiple aberrant immunophenotypes including defective antigen presenting cell immunoregulatory functions, defects in the regulation of the T lymphocyte repertoire, defective NK cell function, defective cytokine production from macrophages (Fan et al., 2004) and impaired wound healing. They also lack hemolytic complement, C5. NOD mice also are severely hard-of-hearing. A variety of mutations causing immunodeficiencies, targeted mutations in cytokine genes, as well as transgenes affecting immune functions, have been backcrossed into the NOD inbred strain background.

In some aspects of the present disclosure, an immunodeficient mouse provided herein based on the NOD background may have a genotype selected from NOD-Cg-Prkdc$^{scid}$ IL2rg$^{tm1wJ1}$SzJ (NSG™), a NOD.Cg-Rag1$^{tm1Mom}$ Il2rg1$^{tm1Wjl}$/SzJ (NRG), and NOD.Cg-Prkdc$^{scid}$Il2rg$^{tm1Sug}$/ShiJic (NOG). Other immunodeficient mouse strains are contemplated herein.

In some embodiments, an immunodeficient mouse model has an NSG™ genotype. The NSG™ mouse (e.g., Jackson Labs Stock No.: #005557) is an immunodeficient mouse that lacks mature T cells, B cells, and NK cells, is deficient in multiple cytokine signaling pathways, and has many defects in innate immune immunity (see, e.g., Shultz, Ishikawa, & Greiner, 2007; Shultz et al., 2005; and Shultz et al., 1995, each of which is incorporated herein by reference). The NSG™ mouse, derived from the NOD mouse strain NOD/ShiLtJ (see, e.g., Makino et al., 1980, which is incorporated herein by reference), includes the Prkdc$^{scid}$ mutation (also referred to as the "severe combined immunodeficiency" mutation or the "scid" mutation) and the Il2rg$^{tm1Wjl}$ targeted mutation. The Prkdc$^{scid}$ mutation is a loss-of-function (null) mutation in the mouse homolog of the human PRKDC gene—this mutation essentially eliminates adaptive immunity (see, e.g., (Blunt et al., 1995; Greiner, Hesselton, & Shultz, 1998), each of which is incorporated herein by reference). The Il2rg$^{tm1Wjl}$ mutation is a null mutation in the gene encoding the interleukin 2 receptor gamma chain (IL2Rγ, homologous to IL2RG in humans), which blocks NK cell differentiation, thereby removing an obstacle that prevents the efficient engraftment of primary human cells (Cao et al., 1995; Greiner et al., 1998; and Shultz et al., 2005, each of which is incorporated herein by reference).

In some embodiments, an immunodeficient mouse model has an NRG genotype. The NRG mouse (e.g., Jackson Labs Stock #007799) is extremely immunodeficient. This mouse comprises two mutations on the NOD/ShiLtJ genetic background; a targeted knockout mutation in recombination activating gene 1 (Rag1) and a complete null allele of the IL2 receptor common gamma chain (IL2rg$^{null}$). The Rag1$^{null}$ mutation renders the mice B and T cell deficient and the IL2rg$^{null}$ mutation prevents cytokine signaling through multiple receptors, leading to a deficiency in functional NK cells. The extreme immunodeficiency of NRG allows the mice to be humanized by engraftment of human CD34+ hematopoietic stem cells (HSC) and patient derived xenografts (PDXs) at high efficiency. The immunodeficient NRG mice are more resistant to irradiation and genotoxic drugs than mice with a scid mutation in the DNA repair enzyme Prkdc.

In some embodiments, an immunodeficient mouse model is an NOG mouse. The NOG mouse (Ito M et al., Blood 2002) is an extremely severe combined immunodeficient (scid) mouse established by combining the NOD/scid mouse and the IL-2 receptor-γ chain knockout (IL2rγKO) mouse (Ohbo K. et al., Blood 1996). The NOG mouse lacks T and B cells, lacks natural killer (NK) cells, exhibits reduced dendritic cell function and reduced macrophage function, and lacks complement activity.

In some embodiments, an immunodeficient mouse model has an NCG genotype. The NCG mouse (e.g., Charles River Stock #572) was created by sequential CRISPR/Cas9 editing of the Prkdc and Il2rg loci in the NOD/Nju mouse, generating a mouse coisogenic to the NOD/Nju. The NOD/Nju carries a mutation in the Sirpa (SIRPα) gene that allows for engrafting of foreign hematopoietic stem cells. The Prkdc knockout generates a SCID-like phenotype lacking proper T-cell and B-cell formation. The knockout of the Il2rg gene further exacerbates the SCID-like phenotype while additionally resulting in a decrease of NK cell production.

Provided herein, in some embodiments, are immunodeficient mouse models that are deficient in MHC Class I, MHC Class II, or MHC Class I and MHC Class II. A mouse that is deficient in MHC Class I and/or MHC Class II does not express the same level of MHC Class I proteins (e.g., α-microglobulin and β2-microglobulin (B2M)) and/or MHC Class II proteins (e.g., α chain and β chain) or does not have the same level of MHC Class I and/or MHC Class II protein activity as a non-immunodeficient (e.g., MHC Class I/II wild-type) mouse. In some embodiments, the expression or activity of MHC Class I and/or MHC Class II proteins is reduced (e.g., by at least 30%, at least 40%, at least 50%, at least 60%, at least 70%, at least 80%, at least 90% or more), relative to a non-immunodeficient mouse.

Immunodeficient mice that are deficient in MHC Class I, MHC Class II, and MHC Class I and MHC Class II are described in International Publication No. WO 2018/209344, the contents of which are incorporated by reference herein.

The terms "MHC Class I" and "MHC I" are used interchangeably herein and refer to a complex formed by MHC I α protein and β2-microglobulin. MHC Class I α proteins includes an extracellular domain with the subdomains α1, α2, and α3, a transmembrane domain, and a cytoplasmic tail. The terms "H2-K", "H2-D", and "H2-L" refer to MHC Class I α protein subclasses, all of which are encoded on mouse chromosome 17. β2-microglobulin associates non-covalently with the α3 subdomain of MHC I α protein. The gene encoding mouse β2-microglobulin is encoded on mouse chromosome 2.

The terms "MHC Class II" and "MHC II" are used interchangeably to refer to a complex formed by two non-covalently associated proteins: an MHC II α protein and an MHC II β protein. The terms "H-2A" and "H-2E" (often abbreviated as I-A and I-E, respectively) refer to subclasses of MHC II. The MHC II α protein and MHC II β proteins span the plasma membrane and each contains an extracellular domain, a transmembrane domain, and a cytoplasmic domain. The extracellular portion of the MHC II α protein includes MHC II α1 and MHC II α2 domains, and the extracellular portion of the MHC II β protein includes MHC II β1 and MHC II β2 domains.

In some embodiments, an immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (abbreviated as NSG-(K$^b$ D$^b$)$^{null}$ (IA$^{null}$)). The NSG-(K$^b$ D$^b$)$^{null}$ (IA$^{null}$) mouse lacks functional MHC I due to a homozygous null mutation of H2-K and H2-D MHC I α protein subclasses (abbreviated (K$^b$ D$^b$)$^{null}$). The NSG-(K$^b$ D$^b$)$^{null}$ (IA$^{null}$) mouse lacks functional MHC II due to a homozygous null mutation of H-2A subclass of MHC II (abbreviated as IA$^{null}$).

In some embodiments, an immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg(Ins2-HBEGF)6832Ugfm/Sz (abbreviated as NSG-B2M$^{null}$ (IA IE)$^{null}$) mouse. The NSG-B2M$^{null}$ (IA IE)$^{null}$ mouse lacks functional MHC I due to a homozygous null mutation of β2 microglobulin (abbreviated B2M$^{null}$). The NSG-B2M$^{null}$(IA IE)$^{null}$ mouse lacks functional MHC II due to a homozygous null mutation of H-2A and H-2E subclasses of MHC II (abbreviated as (IA IE)$^{null}$).

In some embodiments, an immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg(Ins2-HBEGF)6832Ugfm/Sz transgenic mouse, abbreviated as NSG-RIP-DTR (K$^b$ D$^b$)$^{null}$ (IA$^{null}$), which expresses the diphtheria toxin receptor under the control of the rat insulin promoter on an NSG™ background. Injection of diphtheria toxin (DT) into mice expressing the diphtheria toxin receptor under the control of the rat insulin promoter leads to mouse pancreatic beta cell death and hyperglycemia. The NSG-RIP-DTR (K$^b$ D$^b$)$^{null}$ (IA$^{null}$) strain permits the complete and specific ablation of mouse pancreatic beta cells, avoiding the broadly toxic effects of diabetogenic drugs such as streptozotocin.

Humanized Mouse Models

Provided herein, in some embodiments, are humanized immunodeficient mouse models and methods of producing the models. Immunodeficient mice engrafted with functional human cells and/or tissues are referred to as "humanized mice." As used herein, the terms "humanized mouse", "humanized immune deficient mouse", "humanized immunodeficient mouse", and the plural versions thereof are used interchangeably to refer to an immunodeficient mouse humanized by engraftment with functional human cells and/or tissues. For example, mouse models may be engrafted with human hematopoietic stem cells (HSCs) and/or human peripheral blood mononuclear cells (PMBCs). In some embodiments, mouse models are engrafted with human tissues such as islets, liver, skin, and/or solid or hematologic cancers. In other embodiments, mouse models may be genetically modified such that endogenous mouse genes are converted to human homologs (see, e.g., Pearson, et al., Curr Protoc Immunol., 2008, Chapter: Unit-15.21).

Humanized mice are generated by starting with an immunodeficient mouse and, if necessary, depleting and/or suppressing any remaining murine immune cells (e.g., chemically or with radiation). That is, successful survival of the human immune system in the immunodeficient mice may require suppression of the mouse's immune system to prevent GVHD (graft-versus-host disease) rejections. After the immunodeficient mouse's immune system has been sufficiently suppressed, the mouse is engrafted with human cells (e.g., HSCs and/or PBMCs). As used herein, "engraft" refers to the process of the human cells migrating to, and incorporating into, an existing tissue of interest in vivo. With respect to the humanized immunodeficient mouse, the engrafted human cells provide functional mature human cells (e.g., immune cells). The model has a specific time window of about 4-5 weeks after engraftment before GVHD sets in. To increase the longevity of the model, double-knockout mice lacking functional MHC I and MHC II, as described above, may be used.

The engrafted human cells (e.g., HSCs or PMBCs) for humanization, in some embodiments, are human leukocyte-antigen (HLA)-matched to the human cancer cells of the mouse models. HLA-matched refers to cells that express the same major histocompatibility complex (MHC) genes. Engrafting mice with HLA-matched human xenografts and human immune cells, for example, reduces or prevents immunogenicity of the human immune cells. In some embodiments, a humanized mouse provided in the present disclosure is engrafted with human PMBCs or human HSCs that are HLA-matched to a PDX or human cancer cell line.

Irradiation

As described above, in some embodiments, immunodeficient mice are irradiated prior to engraftment with human cells, such as human HSCs and/or PMBCs. It is thought that irradiation of an immunodeficient mouse destroys mouse immune cells in peripheral blood, spleen, and bone marrow, which facilitates engraftment of human cells, such as human HSCs and/or PMBCs (e.g., by increasing human cell survival factors), as well as expansion of other immune cells. Irradiation also shortens the time it takes to accumulate the required number of human immune cells to "humanize" the mouse models.

For immunodeficient mice (e.g., NSG™ mice), this preparation is commonly accomplished through whole-body gamma irradiation. Irradiators may vary in size depending on their intended use. Animals are generally irradiated for short periods of time (less than 15 min). The amount of time spent inside the irradiator varies depending on the radioisotope decay charts, amount of irradiation needed, and source of ionizing energy (that is, X-rays versus gamma rays, for which a cesium or cobalt source is needed).

A myeloablative irradiation dose is usually 700 to 1300 cGy, though in some embodiments, lower doses such as 1-100 cGy (e.g., about 2, 5, or 10 cGy), or 300-700 cGy may be used.

As an example, the mouse may be irradiated with 100 cGy X-ray (or 75 cGy-125 cGy X-ray). In some embodiments, the dose is about 1, 2, 3, 4, 5, 10, 20, 100, 200, 300, 400, 500, 600, 700, 800, 900, 1000, 1100, 1200, or 1300 cGy, or between any of the two recited doses herein, such as 100-300 cGy, 200-500 cGy, 600-1000 cGy, or 700-1300 cGy. In some embodiments, the immunodeficient mouse is irradiated about 15 minutes, 30 minutes, 45 minutes, 1 hour, or more before engraftment with human HSCs and/or PMBCs. In some embodiments, the immunodeficient mouse is engrafted with human HSCs and/or PMBCs 1, 2, 3, 4, 5, 6, 7, 8, 9, 10, 11, 12, 13, 14, 15, 16, 17, or 18 days after irradiation.

Engraftment

As described above, in some embodiments, the irradiated immunodeficient mice are engrafted with HSCs and/or PBMCs, humanizing the mice. Engraftment refers to the process of the human cells migrating to, and incorporating into, an existing tissue of interest in vivo. The PBMCs may be engrafted after irradiation and before engraftment of human cancer cells, after irradiation and concurrently with engraftment of human cancer cells, or after irradiation and after engraftment of human cancer cells.

Peripheral blood mononuclear cells (PBMCs) are peripheral blood cells having a round nucleus. These mononuclear blood cells recirculate between tissues and blood and are a critical component in the immune system to fight infection and adapt to intruders. There are two main types of mononuclear cells, lymphocytes and monocytes. The lymphocyte population of PBMCs typically includes T cells, B cells and NK cells.

PBMCs may be isolated from whole blood samples, for example (e.g., Ficoll gradient). In some embodiments, PBMCs from a subject (e.g., a human subject) with a current or previous diagnosis of a pathogen or pathogenic disease may be used.

Hematopoietic stem cells (HSCs) are the stem cells that give rise to other blood cells during a process referred to as hematopoiesis. Hematopoietic stem cells give rise to different types of blood cells, in lines called myeloid and lymphoid. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, natural killer cells, and innate lymphoid cells.

Methods of engrafting immunodeficient mice with HSCs and/or PBMCs to yield a humanized mouse model include but are not limited to intraperitoneal or intravenous injection (Shultz et al., J Immunol, 2015, 174:6477-6489; Pearson et al., Curr Protoc Immunol. 2008; 15-21; Kim et al., AIDS Res Hum Retrovirus, 2016, 32(2): 194-2020; Yaguchi et al., Cell & Mol Immunol, 2018, 15:953-962). In some embodiments, the mouse is engrafted with $1.0 \times 10^6$-$3.0 \times 10^7$ HSCs and/or PBMCs.

For example, the mouse may be engrafted with $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$, $2.5 \times 10^6$, $3.0 \times 10^6$ or more HSCs and/or PBMCs. In some embodiments, the mouse is engrafted with $1.0$-$1.1 \times 10^6$, $1.0$-$1.2 \times 10^6$, $1.0$-$1.3 \times 10^6$, $1.0$-$1.4 \times 10^6$, $1.0$-$1.5 \times 10^6$, $1.0$-$1.6 \times 10^6$, $1.0$-$1.7 \times 10^6$, $1.0$-$1.8 \times 10^6$, $1.0$-$1.9 \times 10^6$, $1.0$-$2.0 \times 10^6$, $1.0$-$2.25 \times 10^6$, $1.0$-$2.5 \times 10^6$, $1.0$-$2.75 \times 10^6$, $1.0$-$3.0 \times 10^6$, $1.1$-$1.2 \times 10^6$, $1.1$-$1.3 \times 10^6$, $1.1$-$1.4 \times 10^6$, $1.1$-$1.5 \times 10^6$, $1.1$-$1.6 \times 10^6$, $1.1$-$1.7 \times 10^6$, $1.1$-$1.8 \times 10^6$, $1.1$-$1.9 \times 10^6$, $1.1$-$2.0 \times 10^6$, $1.1$-$2.25 \times 10^6$, $1.1$-$2.5 \times 10^6$, $1.1$-$2.75 \times 10^6$, $1.1$-$3.0 \times 10^6$, $1.2$-$1.3 \times 10^6$, $1.2$-$1.4 \times 10^6$, $1.2$-$1.5 \times 10^6$, $1.2$-$1.6 \times 10^6$, $1.2$-$1.7 \times 10^6$, $1.2$-$1.8 \times 10^6$, $1.2$-$1.9 \times 10^6$, $1.2$-$2.0 \times 10^6$, $1.2$-$2.25 \times 10^6$, $1.2$-$2.5 \times 10^6$, $1.2$-$2.75 \times 10^6$, $1.2$-$3.0 \times 10^6$, $1.3$-$1.4 \times 10^6$, $1.3$-$1.5 \times 10^6$, $1.3$-$1.6 \times 10^6$, $1.3$-$1.7 \times 10^6$, $1.3$-$1.8 \times 10^6$, $1.3$-$1.9 \times 10^6$, $1.3$-$2.0 \times 10^6$, $1.3$-$2.25 \times 10^6$, $1.3$-$2.5 \times 10^6$, $1.3$-$2.75 \times 10^6$, $1.3$-$3.0 \times 10^6$, $1.4$-$1.5 \times 10^6$, $1.4$-$1.6 \times 10^6$, $1.4$-$1.7 \times 10^6$, $1.4$-$1.8 \times 10^6$, $1.4$-$1.9 \times 10^6$, $1.4$-$2.0 \times 10^6$, $1.4$-$2.25 \times 10^6$, $1.4$-$2.5 \times 10^6$, $1.4$-$2.75 \times 10^6$, $1.4$-$3.0 \times 10^6$, $1.5$-$1.6 \times 10^6$, $1.5$-$1.7 \times 10^6$, $1.5$-$1.8 \times 10^6$, $1.5$-$1.9 \times 10^6$, $1.5$-$2.0 \times 10^6$, $1.5$-$2.25 \times 10^6$, $1.5$-$2.5 \times 10^6$, $1.5$-$2.75 \times 10^6$, $1.5$-$3.0 \times 10^6$, $1.6$-$1.7 \times 10^6$, $1.6$-$1.8 \times 10^6$, $1.6$-$1.9 \times 10^6$, $1.6$-$2.0 \times 10^6$, $1.6$-$2.25 \times 10^6$, $1.6$-$2.5 \times 10^6$, $1.6$-$2.75 \times 10^6$, $1.6$-$3.0 \times 10^6$, $1.7$-$1.8 \times 10^6$, $1.7$-$1.9 \times 10^6$, $1.7$-$2.0 \times 10^6$, $1.7$-$2.25 \times 10^6$, $1.7$-$2.5 \times 10^6$, $1.7$-$2.75 \times 10^6$, $1.7$-$3.0 \times 10^6$, $1.8$-$1.9 \times 10^6$, $1.8$-$2.0 \times 10^6$, $1.8$-$2.25 \times 10^6$, $1.8$-$2.5 \times 10^6$, $1.8$-$2.75 \times 10^6$, $1.8$-$3.0 \times 10^6$, $1.9$-$2.0 \times 10^6$, $1.9$-$2.25 \times 10^6$, $1.9$-$2.5 \times 10^6$, $1.9$-$2.75 \times 10^6$, $1.9$-$3.0 \times 10^6$, $2.0$-$2.25 \times 10^6$, $2.0$-$2.5 \times 10^6$, $2.0$-$2.75 \times 10^6$, $2.0$-$3.0 \times 10^6$, $2.25$-$2.5 \times 10^6$, $2.25$-$2.75 \times 10^6$, $2.25$-$3.0 \times 10^6$, $2.5$-$2.75 \times 10^6$, $2.5$-$3.0 \times 10^6$, or $2.75$-$3.0 \times 10^6$ HSCs and/or PBMCs.

In some embodiments, the mouse may be engrafted with $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $2.5 \times 10^7$, $3.0 \times 10^7$ or more HSCs and/or PBMCs. In some embodiments, the mouse is engrafted with $1.0$-$1.1 \times 10^7$, $1.0$-$1.2 \times 10^7$, $1.0$-$1.3 \times 10^7$, $1.0$-$1.4 \times 10^7$, $1.0$-$1.5 \times 10^7$, $1.0$-$1.6 \times 10^7$, $1.0$-$1.7 \times 10^7$, $1.0$-$1.8 \times 10^7$, $1.0$-$1.9 \times 10^7$, $1.0$-$2.0 \times 10^7$, $1.0$-$2.25 \times 10^7$, $1.0$-$2.5 \times 10^7$, $1.0$-$2.75 \times 10^7$, $1.0$-$3.0 \times 10^7$, $1.1$-$1.2 \times 10^7$, $1.1$-$1.3 \times 10^7$, $1.1$-$1.4 \times 10^7$, $1.1$-$1.5 \times 10^7$, $1.1$-$1.6 \times 10^7$, $1.1$-$1.7 \times 10^7$, $1.1$-$1.8 \times 10^7$, $1.1$-$1.9 \times 10^7$, $1.1$-$2.0 \times 10^7$, $1.1$-$2.25 \times 10^7$, $1.1$-$2.5 \times 10^7$, $1.1$-$2.75 \times 10^7$, $1.1$-$3.0 \times 10^7$, $1.2$-$1.3 \times 10^7$, $1.2$-$1.4 \times 10^7$, $1.2$-$1.5 \times 10^7$, $1.2$-$1.6 \times 10^7$, $1.2$-$1.7 \times 10^7$, $1.2$-$1.8 \times 10^7$, $1.2$-$1.9 \times 10^7$, $1.2$-$2.0 \times 10^7$, $1.2$-$2.25 \times 10^7$, $1.2$-$2.5 \times 10^7$, $1.2$-$2.75 \times 10^7$, $1.2$-$3.0 \times 10^7$, $1.3$-$1.4 \times 10^7$, $1.3$-$1.5 \times 10^7$, $1.3$-$1.6 \times 10^7$, $1.3$-$1.7 \times 10^7$, $1.3$-$1.8 \times 10^7$, $1.3$-$1.9 \times 10^7$, $1.3$-$2.0 \times 10^7$, $1.3$-$2.25 \times 10^7$, $1.3$-$2.5 \times 10^7$, $1.3$-$2.75 \times 10^7$, $1.3$-$3.0 \times 10^7$, $1.4$-$1.5 \times 10^7$, $1.4$-$1.6 \times 10^7$, $1.4$-$1.7 \times 10^7$, $1.4$-$1.8 \times 10^7$, $1.4$-$1.9 \times 10^7$, $1.4$-$2.0 \times 10^7$, $1.4$-$2.25 \times 10^7$, $1.4$-$2.5 \times 10^7$, $1.4$-$2.75 \times 10^7$, $1.4$-$3.0 \times 10^7$, $1.5$-$1.6 \times 10^7$, $1.5$-$1.7 \times 10^7$, $1.5$-$1.8 \times 10^7$, $1.5$-$1.9 \times 10^7$, $1.5$-$2.0 \times 10^7$, $1.5$-$2.25 \times 10^7$, $1.5$-$2.5 \times 10^7$, $1.5$-$2.75 \times 10^7$, $1.5$-$3.0 \times 10^7$, $1.6$-$1.7 \times 10^7$, $1.6$-$1.8 \times 10^7$, $1.6$-$1.9 \times 10^7$, $1.6$-$2.0 \times 10^7$, $1.6$-$2.25 \times 10^7$, $1.6$-$2.5 \times 10^7$, $1.6$-$2.75 \times 10^7$, $1.6$-$3.0 \times 10^7$, $1.7$-$1.8 \times 10^7$, $1.7$-$1.9 \times 10^7$, $1.7$-$2.0 \times 10^7$, $1.7$-$2.25 \times 10^7$, $1.7$-$2.5 \times 10^7$, $1.7$-$2.75 \times 10^7$, $1.7$-$3.0 \times 10^7$, $1.8$-$1.9 \times 10^7$, $1.8$-$2.0 \times 10^7$, $1.8$-$2.25 \times 10^7$, $1.8$-$2.5 \times 10^7$, $1.8$-$2.75 \times 10^7$, $1.8$-$3.0 \times 10^7$, $1.9$-$2.0 \times 10^7$, $1.9$-$2.25 \times 10^7$, $1.9$-$2.5 \times 10^7$, $1.9$-$2.75 \times 10^7$, $1.9$-$3.0 \times 10^7$, $2.0$-$2.25 \times 10^7$, $2.0$-$2.5 \times 10^7$, $2.0$-$2.75 \times 10^7$, $2.0$-$3.0 \times 10^7$, $2.25$-$2.5 \times 10^7$, $2.25$-$2.75 \times 10^7$, $2.25$-$3.0 \times 10^7$, $2.5$-$2.75 \times 10^7$, $2.5$-$3.0 \times 10^7$, or $2.75$-$3.0 \times 10^7$ HSCs and/or PBMCs. In some embodiments, the mouse is engrafted with $2 \times 10^7$ HSCs and/or PBMCs. According to some embodiments, the mouse is engrafted with $4.5$-$5.5 \times 10^7$ ($4.5$-$5.0 \times 10^7$, $5.0$-$5.5 \times 10^7$) HSCs and/or PBMCs.

Nucleic Acids: Engineering and Delivery

The nucleic acids provided herein, in some embodiments, are engineered. An engineered nucleic acid is a nucleic acid (e.g., at least two nucleotides covalently linked together, and in some instances, containing phosphodiester bonds, referred to as a phosphodiester backbone) that does not occur in nature. Engineered nucleic acids include recombinant nucleic acids and synthetic nucleic acids. A recombinant nucleic acid is a molecule that is constructed by joining nucleic acids (e.g., isolated nucleic acids, synthetic nucleic acids or a combination thereof) from two different organisms (e.g., human and mouse). A synthetic nucleic acid is a molecule that is amplified or chemically, or by other means, synthesized. A synthetic nucleic acid includes those that are chemically modified, or otherwise modified, but can base pair with (bind to) naturally occurring nucleic acid molecules. Recombinant and synthetic nucleic acids also include those molecules that result from the replication of either of the foregoing.

An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

In some embodiments, a nucleic acid is a complementary DNA (cDNA). cDNA is synthesized from a single-stranded RNA (e.g., messenger RNA (mRNA) or microRNA (miRNA)) template in a reaction catalyzed by reverse transcriptase.

Engineered nucleic acids of the present disclosure may be produced using standard molecular biology methods (see, e.g., *Green and Sambrook, Molecular Cloning,* A Laboratory Manual, 2012, Cold Spring Harbor Press). In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids may be used in accordance with the present disclosure.

A gene is a distinct sequence of nucleotides, the order of which determines the order of monomers in a polynucleotide or polypeptide. A gene typically encodes a protein. A gene may be endogenous (occurring naturally in a host organism) or exogenous (transferred, naturally or through genetic engineering, to a host organism). An allele is one of two or more alternative forms of a gene that arise by mutation and are found at the same locus on a chromosome. A gene, in some embodiments, includes a promoter sequence, coding regions (e.g., exons), non-coding regions (e.g., introns), and regulatory regions (also referred to as regulatory sequences).

A mouse comprising a human gene is considered to comprise a human transgene. A transgene is a gene exogenous to a host organism. That is, a transgene is a gene that has been transferred, naturally or through genetic engineering, to a host organism. A transgene does not occur naturally in the host organism (the organism, e.g., mouse, comprising the transgene).

A promoter is a nucleotide sequence to which RNA polymerase binds to initial transcription (e.g., ATG). Promoters are typically located directly upstream from (at the 5' end of) a transcription initiation site. In some embodiments, a promoter is an endogenous promoter. An endogenous promoter is a promoter that naturally occurs in that host animal.

An open reading frame is a continuous stretch of codons that begins with a start codon (e.g., ATG), ends with a stop codon (e.g., TAA, TAG, or TGA), and encodes a polypeptide, for example, a protein. An open reading frame is operably linked to a promoter if that promoter regulates transcription of the open reading frame.

An exon is a region of a gene that codes for amino acids. An intron (and other non-coding DNA) is a region of a gene that does not code for amino acids.

A nucleotide sequence encoding a product (e.g., protein), in some embodiments, has a length of 200 base pairs (bp) to 100 kilobases (kb). The nucleotide sequence, in some embodiments, has a length of at least 10 kb. For example, the nucleotide sequence may have a length of at least 15 kb, at least 20 kb, at least 25 kb, at least 30 kb, or at least 35 kb. In some embodiments, the nucleotide sequence has a length of 10 to 100 kb, 10 to 75 kb, 10 to 50 kb, 10 to 30 kb, 20 to 100 kb, 20 to 75 kb, 20 to 50 kb, 20 to 30 kb, 30 to 100 kb, 30 to 75 kb, or 30 to 50 kb.

Any one of the nucleic acids provided herein may have a length of 200 bp to 500 kb, 200 bp to 250 kb, or 200 bp to 100 kb. A nucleic acid, in some embodiments, has a length of at least 10 kb. For example, a nucleic acid may have a length of at least 15 kb, at least 20 kb, at least 25 kb, at least 30 kb, at least 35 kb, at least 50 kb, at least 100 kb, at least 200 kb, at least 300 kb, at least 400 kb, or at least 500 kb. In some embodiments, a nucleic acid has a length of 10 to 500 kb, 20 to 400 kb, 10 to 300 kb, 10 to 200 kb, or 10 to 100 kb. In some embodiments, a nucleic acid has a length of 10 to 100 kb, 10 to 75 kb, 10 to 50 kb, 10 to 30 kb, 20 to 100 kb, 20 to 75 kb, 20 to 50 kb, 20 to 30 kb, 30 to 100 kb, 30 to 75 kb, or 30 to 50 kb. A nucleic acid may be circular or linear.

The nucleic acids described herein, in some embodiments, include a modification. A modification, with respect to a nucleic acid, is any manipulation of the nucleic acid, relative to the corresponding wild-type nucleic acid (e.g., the naturally-occurring nucleic acid). A genomic modification is thus any manipulation of a nucleic acid in a genome (e.g., in a coding region, non-coding region, and/or regulatory region), relative to the corresponding wild-type nucleic acid (e.g., the naturally-occurring (unmodified) nucleic acid) in the genome. Non-limiting examples of nucleic acid (e.g., genomic) modifications include deletions, insertions, "indels" (deletion and insertion), and substitutions (e.g., point mutations). In some embodiments, a deletion, insertion, indel, or other modification in a gene results in a frameshift mutation such that the gene no longer encodes a functional product (e.g., protein). Modifications also include chemical modifications, for example, chemical modifications of at least one nucleobase. Methods of nucleic acid modification, for example, those that result in gene inactivation, are known and include, without limitation, RNA interference, chemical modification, and gene editing (e.g., using recombinases or other programmable nuclease systems, e.g., CRISPR/Cas, TALENs, and/or ZFNs).

A nucleic acid, such as an allele or alleles of a gene, may be modified such that it does not produce a detectable level of a functional gene product (e.g., a functional protein). Thus, an inactivated allele is an allele that does not produce a detectable level of a functional gene product (e.g., a functional protein). A detectable level of a protein is any level of protein detected using a standard protein detection assay, such as flow cytometry and/or an ELISA. In some embodiments, an inactivated allele is not transcribed. In some embodiments, an inactivated allele does not encode a functional protein.

Vectors used for delivery of a nucleic acid include minicircles, plasmids, bacterial artificial chromosomes (BACs), and yeast artificial chromosomes. It should be understood, however, that a vector may not be needed. For example, a circularized or linearized nucleic acid may be delivered to an embryo without its vector backbone. Vector backbones are small (~ 4 kb), while donor DNA to be circularized can range from >100 bp to 50 kb, for example.

Methods for delivering nucleic acids to mouse embryos for the production of transgenic mice include, but are not limited to, electroporation (see, e.g., Wang W et al. *J Genet Genomics* 2016; 43(5):319-27; WO 2016/054032; and WO 2017/124086, each of which is incorporated herein by reference), DNA microinjection (see, e.g., Gordon and Ruddle, *Science* 1981: 214: 1244-124, incorporated herein by reference), embryonic stem cell-mediated gene transfer (see, e.g., Gossler et al., *Proc. Natl. Acad. Sci.* 1986; 83: 9065-9069, incorporated herein by reference), and retrovirus-mediated gene transfer (see, e.g., Jaenisch, *Proc. Natl. Acad. Sci.* 1976; 73: 1260-1264, incorporated herein by reference), any of which may be used as provided herein.

Genomic Editing Methods

Engineered nucleic acids, such as guide RNAs, donor polynucleotides, and other nucleic acid coding sequences, for example, may be introduced to a genome of an embryo using any suitable method. The present application contemplates the use of a variety of gene editing technologies, for example, to introduce nucleic acids into the genome of an embryo to produce a transgenic rodent. Non-limiting examples include programmable nuclease-based systems, such as clustered regularly interspaced short palindromic repeat (CRISPR) systems, zinc-finger nucleases (ZFNs), and transcription activator-like effector nucleases (TALENs). See, e.g., Carroll D *Genetics.* 2011; 188(4): 773-782; Joung J K et al. *Nat Rev Mol Cell Biol.* 2013; 14(1): 49-55; and Gaj T et al. *Trends Biotechnol.* 2013 July; 31(7): 397-405, each of which is incorporated by reference herein.

In some embodiments, a CRISPR system is used to edit the genome of mouse embryos provided herein. See, e.g., Harms D W et al., *Curr Protoc Hum Genet.* 2014; 83: 15.7.1-15.7.27; and Inui M et al., *Sci Rep.* 2014; 4: 5396, each of which are incorporated by reference herein). For example, Cas9 mRNA or protein, one or multiple guide RNAs (gRNAs), and/or a donor nucleic acid can be delivered, e.g., injected or electroporated, directly into mouse embryos at the one-cell (zygote) stage or a later stage to facilitate homology directed repair (HDR), for example, to introduce an engineered nucleic acid (e.g., donor nucleic acid) into the genome.

The CRISPR/Cas system is a naturally occurring defense mechanism in prokaryotes that has been repurposed as an RNA-guided-DNA-targeting platform for gene editing. Engineered CRISPR systems contain two main components: a guide RNA (gRNA) and a CRISPR-associated endonuclease (e.g., Cas protein). The gRNA is a short synthetic RNA composed of a scaffold sequence for nuclease-binding and a user-defined nucleotide spacer (e.g., ~15-25 nucleotides, or ~20 nucleotides) that defines the genomic target (e.g., gene) to be modified. Thus, one can change the genomic target of the Cas protein by simply changing the target sequence present in the gRNA. In some embodiments, the Cas9 endonuclease is from *Streptococcus pyogenes* (NGG PAM) or *Staphylococcus aureus* (NNGRRT or NNGRR(N) PAM), although other Cas9 homologs, orthologs, and/or variants (e.g., evolved versions of Cas9) may be used, as provided herein. Additional non-limiting examples of RNA-guided nucleases that may be used as provided herein include Cpf1 (TTN PAM); SpCas9 D1135E variant (NGG (reduced NAG binding) PAM); SpCas9 VRER variant (NGCG PAM); SpCas9 EQR variant (NGAG PAM); SpCas9 VQR variant (NGAN or NGNG PAM); *Neisseria meningitidis* (NM) Cas9 (NNNNGATT PAM); *Streptococcus thermophilus* (ST) Cas9 (NNAGAAW PAM); and *Treponema denticola* (TD) Cas9 (NAAAAC). In some embodiments, the CRISPR-associated endonuclease is selected from Cas9, Cpf1, C2c1, and C2c3. In some embodiments, the Cas nuclease is Cas9.

A guide RNA comprises at least a spacer sequence that hybridizes to (binds to) a target nucleic acid sequence and a CRISPR repeat sequence that binds the endonuclease and guides the endonuclease to the target nucleic acid sequence. As is understood by the person of ordinary skill in the art, each gRNA is designed to include a spacer sequence complementary to its genomic target sequence. See, e.g., Jinek et al., *Science,* 2012; 337: 816-821 and Deltcheva et al., *Nature,* 2100; 471: 602-607, each of which is incorporated by reference herein.

In some embodiments, the RNA-guided nuclease and the gRNA are complexed to form a ribonucleoprotein (RNP), prior to delivery to an embryo.

The concentration of RNA-guided nuclease or nucleic acid encoding the RNA-guided nuclease may vary. In some embodiments, the concentration is 100 ng/µl to 1000 ng/µl. For example, the concentration may be 100, 150, 200, 250, 300, 350, 400, 450, 500, 550, 600, 650, 700, 750, 800, 850, 900, 950, or 1000 ng/µl. In some embodiments, the concentration is 100 ng/µl to 500 ng/µl, or 200 ng/µl to 500 ng/µl.

The concentration of gRNA may also vary. In some embodiments, the concentration is 200 ng/µl to 2000 ng/µl. For example, the concentration may be 200, 300, 400, 500, 600, 700, 800, 900, 1000, 1100, 1200, 1300, 1400, 1500, 1600, 1700, 1700, 1900, or 2000 ng/µl. In some embodiments, the concentration is 500 ng/µl to 1000 ng/µl. In some embodiments, the concentration is 100 ng/µl to 1000 ng/µl. For example, the concentration may be 100, 150, 200, 250, 300, 350, 400, 450, 500, 550, 600, 650, 700, 750, 800, 850, 900, 950, or 1000 ng/µl.

In some embodiments, the ratio of concentration of RNA-guided nuclease or nucleic acid encoding the RNA-guided nuclease to the concentration of gRNA is 2:1. In other embodiments, the ratio of concentration of RNA-guided nuclease or nucleic acid encoding the RNA-guided nuclease to the concentration of gRNA is 1:1.

A donor nucleic acid typically includes a sequence of interest flanked by homology arms. Homology arms are regions of the ssDNA that are homologous to regions of genomic DNA located in a genomic locus. One homology arm is located to the left (5') of a genomic region of interest (into which a sequence of interest is introduced) (the left homology arm) and another homology arm is located to the right (3') of the genomic region of interest (the right homology arm). These homology arms enable homologous recombination between the ssDNA donor and the genomic locus, resulting in insertion of the sequence of interest into the genomic locus of interest (e.g., via CRISPR/Cas9-mediated homology directed repair (HDR)).

The homology arms may vary in length. For example, each homology arm (the left arm and the right homology arm) may have a length of 20 nucleotide bases to 1000 nucleotide bases. In some embodiments, each homology arm has a length of 20 to 200, 20 to 300, 20 to 400, 20 to 500, 20 to 600, 20 to 700, 20 to 800, or 20 to 900 nucleotide bases. In some embodiments, each homology arm has a length of 20, 30, 40, 50, 60, 70, 80, 90, 100, 150, 200, 250, 300, 350, 400, 450, 500, 550, 600, 650, 700, 750, 800, 850, 900, 950, or 1000 nucleotide bases. In some embodiments, the length of one homology arm differs from the length of the other homology arm. For example, one homology arm may have a length of 20 nucleotide bases, and the other homology arm may have a length of 50 nucleotide bases. In some embodiments, the donor DNA is single stranded. In some embodiments, the donor DNA is double stranded. In some embodiments, the donor DNA is modified, e.g., via phosphorothioation. Other modifications may be made.

Methods of Use

The mouse models of the present disclosure may be used, in some embodiments, to assess the half-life of a therapeutic antibody or other therapeutic protein. Thus, in some embodiments, a method comprising administering to the mouse model a therapeutic antibody (or other therapeutic protein) and assaying half-life of the antibody in a biological sample from the mouse.

The elimination half-life (e.g., serum half-life) of a drug is a pharmacokinetic parameter that is defined as the time it takes for the concentration of the drug in the plasma or the total amount in the body to be reduced by 50%. Thus, after one half-life, the concentration of the drug in the body will be half of the starting dose. For example, if a 100 mg dose of a drug with a half-life of 15 minute is administered intravenously, 15 minutes after administration, 50 mg of the drug remains in the body. In general, the effect of the drug is considered to have a negligible therapeutic effect after 4 half-lives, that is, when only 6.25% of the original dose remains in the body.

The mouse models of the present disclosure may also or alternatively be used, in some embodiments, to identify candidate therapeutic antibodies with desirable therapeutic properties. Non-limiting examples of desirable therapeutic properties include long half-life (≥7 days, see, e.g., Ryman and Meibohm, Pharmacokinetics of monoclonal antibodies, *CPT Pharmacometrics Syst Pharmacol,* 2017, 6(9): 576-

588), low immunogenicity, specific binding to target molecules, solubility in the body, and conformational stability.

Non-limiting examples of routes of administration include intravenous, intraperitoneal, subcutaneous, and intramuscular. Other routes of administration are encompassed by the present disclosure.

A biological sample, in some embodiments, is a blood sample, such as a serum or plasma sample. Other biological samples are encompassed by the present disclosure.

Non-limiting examples of methods for assaying half-life of a therapeutic protein include enzyme linked immunosorbent assay (ELISA), surface plasmon resonance (SPR), radioimmunoassay, chemiluminescent immunoassay, and immunoradiometric assay. Other methods of measuring protein levels in a biological sample are encompassed by the present disclosure.

The therapeutic protein, in some embodiments, is an antibody, such as a monoclonal antibody. In some embodiments, an antibody is a human antibody. In some embodiments, an antibody is a humanized antibody. Humanized antibodies combine a human antibody with a small part of a mouse or rat monoclonal antibody. In some embodiments, an antibody is a chimeric antibody. Chimeric antibodies are structural chimeras made by fusing variable regions from one species (e.g., a mouse) with the constant regions from another species (e.g., a human).

An IgG antibody is one example of an antibody that may be assessed using the mouse models provided herein. For example, the antibody may be an IgG1, IgG2, IgG3, or IgG4 antibody. In some embodiments, the therapeutic antibody is a monoclonal antibody, for example, a monoclonal IgG antibody.

In some embodiments, the mouse models provided herein are used to assess PK behavior of preclinical antibody and/or human Fc fusion candidates. Assessment of other preclinical protein candidates is also contemplated herein.

Non-limiting examples of antibodies that may be assessed using the models of the present disclosure include abagovomab, abciximab, abituzumab, abrezekimab, abrilumab, actoxumab, adalimumab, adecatumumab, aducanumab, afasevikumab, afelimomab, alacizumab pegol, alemtuzumab, alirocumab, altumomab pentetate, amatuximab, amivantamab, anatumomab mafenatox, andecaliximab, anetumab ravtansine, anifrolumab, anrukinzumab, apolizumab, aprutumab ixadotin, arcitumomab, ascrinvacumab, aselizumab, atezolizumab, atidortoxumab, atinumab, atoltivimab, atoltivimab/maftivimab/odesivimab, atorolimumab, avelumab, azintuxizumab vedotin, bapineuzumab, basiliximab, bavituximab, bectumomab, begelomab, belantamab mafodotin, belimumab, bemarituzumab, benralizumab, berlimatoxumab, bermekimab, bersanlimab, bertilimumab, besilesomab, bevacizumab, bezlotoxumab, biciromab, bimagrumab, bimekizumab, birtamimab, bivatuzumab, blesclumab, blinatumomab, blontuvetmab, blosozumab, bococizumab, brazikumab, brentuximab vedotin, briakinumab, brodalumab, brolucizumab, brontictuzumab, burosumab, cabiralizumab, camidanlumab tesirine, camrelizumab, canakinumab, cantuzumab mertansine, cantuzumab ravtansine, caplacizumab, capromab, carlumab, carotuximab, catumaxomab, cedelizumab, cemiplimab, cergutuzumab amunaleukin, certolizumab pegol, cetrelimab, cetuximab, cibisatamab, cirmtuzumab, citatuzumab bogatox, cixutumumab, clazakizumab, cleneliximab, clivatuzumab tetraxetan, codrituzumab, cofetuzumab pelidotin, coltuximab ravtansine, conatumumab, concizumab, cosfroviximab, crenezumab, crizanlizumab, crotedumab, cusatuzumab, dacetuzumab, daclizumab, dalotuzumab, dapirolizumab pegol, daratumumab, dectrekumab, demcizumab, denintuzumab mafodotin, denosumab, depatuxizumab mafodotin, derlotuximab biotin, detumomab, dezamizumab, dinutuximab, dinutuximab beta, diridavumab, domagrozumab, dorlimomab aritox, dostarlimab, drozitumab, duligotuzumab, dupilumab, durvalumab, dusigitumab, duvortuxizumab, ecromeximab, cculizumab, edobacomab, edrecolomab, cfalizumab, efungumab, eldelumab, elezanumab, elgemtumab, clotuzumab, elsilimomab, emactuzumab, emapalumab, emibetuzumab, emicizumab, enapotamab vedotin, enavatuzumab, enfortumab vedotin, enlimomab pegol, enoblituzumab, enokizumab, enoticumab, ensituximab, cpitumomab cituxetan, epratuzumab, eptinezumab, erenumab, erlizumab, ertumaxomab, ctaracizumab, etigilimab, etrolizumab, evinacumab, cvolocumab, exbivirumab, fanolesomab, faralimomab, faricimab, farletuzumab, fasinumab, fbta, felvizumab, fezakinumab, fibatuzumab, ficlatuzumab, figitumumab, firivumab, flanvotumab, fletikumab, flotetuzumab, fontolizumab, foralumab, foravirumab, fremanczumab, fresolimumab, frovocimab, frunevetmab, fulranumab, futuximab, galcanczumab, galiximab, gancotamab, ganitumab, gantenerumab, gatipotuzumab, gavilimomab, gedivumab, gemtuzumab ozogamicin, gevokizumab, gilvetmab, gimsilumab, girentuximab, glembatumumab vedotin, golimumab, gomiliximab, gosuranemab, guselkumab, ianalumab, ibalizumab, ibi, ibritumomab tiuxetan, icrucumab, idarucizumab, ifabotuzumab, igovomab, iladatuzumab vedotin, imab, imalumab, imaprelimab, imciromab, imgatuzumab, inclacumab, indatuximab ravtansine, indusatumab vedotin, inebilizumab, infliximab, intetumumab, inolimomab, inotuzumab ozogamicin, ipilimumab, iratumumab, isatuximab, iscalimab, istiratumab, itolizumab, ixckizumab, keliximab, labctuzumab, lacnotuzumab, ladiratuzumab vedotin, lampalizumab, lanadelumab, landogrozumab, laprituximab emtansine, larcaviximab, lebrikizumab, lemalesomab, lendalizumab, lenvervimab, lenzilumab, lerdelimumab, leronlimab, lesofavumab, letolizumab, lexatumumab, libivirumab, lifastuzumab vedotin, ligelizumab, loncastuximab tesirine, losatuxizumab vedotin, lilotomab satetraxetan, lintuzumab, lirilumab, lodelcizumab, lokivetmab, lorvotuzumab mertansine, lucatumumab, lulizumab pegol, lumiliximab, lumretuzumab, lupartumab, lupartumab amadotin, lutikizumab, maftivimab, mapatumumab, margetuximab, marstacimab, maslimomab, mavrilimumab, matuzumab, mepolizumab, metelimumab, milatuzumab, minretumomab, mirikizumab, mirvetuximab soravtansine, mitumomab, modotuximab, mogamulizumab, monalizumab, morolimumab, mosunetuzumab, motavizumab, moxetumomab pasudotox, muromonab-cd, nacolomab tafenatox, namilumab, naptumomab estafenatox, naratuximab emtansine, narnatumab, natalizumab, navicixizumab, navivumab, naxitamab, nebacumab, necitumumab, nemolizumab, neod, nerelimomab, nesvacumab, netakimab, nimotuzumab, nirscvimab, nivolumab, nofetumomab merpentan, obiltoxaximab, obinutuzumab, ocaratuzumab, ocrelizumab, odesivimab, odulimomab, ofatumumab, olaratumab, oleclumab, olendalizumab, olokizumab, omalizumab, omburtamab, oms, onartuzumab, ontuxizumab, onvatilimab, opicinumab, oportuzumab monatox, oregovomab, orticumab, otelixizumab, otilimab, otlertuzumab, oxclumab, ozanczumab, ozoralizumab, pagibaximab, palivizumab, pamrevlumab, panitumumab, pankomab, panobacumab, parsatuzumab, pascolizumab, pasotuxizumab, pateclizumab, patritumab, pdr, pembrolizumab, pemtumomab, perakizumab, pertuzumab, pexelizumab, pidilizumab, pinatuzumab vedotin, pintumomab, placulumab, prezalumab, plozalizumab, pogalizumab, polatuzumab vedotin, ponczumab, porgaviximab, prasinezumab, prezalizumab, priliximab, pritoxaximab, pritumumab, quilizumab, racotumomab, radretumab, rafivirumab, ralpancizumab, ramucirumab, ranevetmab, ranibizumab, raxibacumab, ravagalimab, ravulizumab, refanezumab, regavirumab, relatlimab, remtolumab, reslizumab, rilotumumab, rinucumab, risankizumab, rituximab, rivabazumab pegol, robatumumab, rmab, roledumab, romilkimab, romosozumab, rontalizumab, rosmantuzumab, rovalpituzumab tesirine, rovelizumab, rozanolixizumab, ruplizumab, sacituzumab govitecan, samalizumab, samrotamab vedotin, sarilumab, satralizumab, satumomab pendetide, secukinumab, selicrelumab, scribantumab, setoxaximab, setrusumab, sevirumab, sibrotuzumab, sifalimumab, siltuximab, simtuzumab, siplizumab, sirtratumab vedotin, sirukumab, sofituzumab vedotin, solanczumab, solitomab, sonepcizumab, sontuzumab, spartalizumab, stamulumab, sulesomab, suptavumab, sutimlimab, suvizumab, suvratoxumab, tabalumab, tacatuzumab tetraxetan, tadocizumab, tafasitamab, talacotuzumab, talizumab, talquetamab, tamtuvetmab, tanczumab, taplitumomab paptox, tarextumab, tavolimab, teclistamab, tefibazumab, telimomab aritox, telisotuzumab, telisotuzumab vedotin, tenatumomab, teneliximab, teplizumab, tepoditamab, teprotumumab, tesidolumab, tetulomab, tezepelumab, tibulizumab, tildrakizumab, tigatuzumab, timigutuzumab, timolumab, tiragolumab, tiragotumab, tislelizumab, tisotumab vedotin, tocilizumab, tomuzotuximab, toralizumab, tosatoxumab, tositumomab, tovetumab, tralokinumab, trastuzumab, trastuzumab duocarmazine, trastuzumab emtansine, tregalizumab, tremelimumab, trevogrumab, tucotuzumab celmoleukin, tuvirumab, ublituximab, ulocuplumab, urelumab, urtoxazumab, ustekinumab, utomilumab, vadastuximab talirine, vanalimab, vandortuzumab vedotin, vantictumab, vanucizumab, vapaliximab, varisacumab, varlilumab, vatelizumab, vedolizumab, veltuzumab, vepalimomab, vesencumab, visilizumab, vobarilizumab, volociximab, vonlerolizumab, vopratelimab, vorsetuzumab mafodotin, votumumab, vunakizumab, xentuzumab, xmab-, zalutumumab, zanolimumab, zatuximab, zenocutuzumab, ziralimumab, zolbetuximab, and zolimomab aritox.

EXAMPLES

Figure 2:
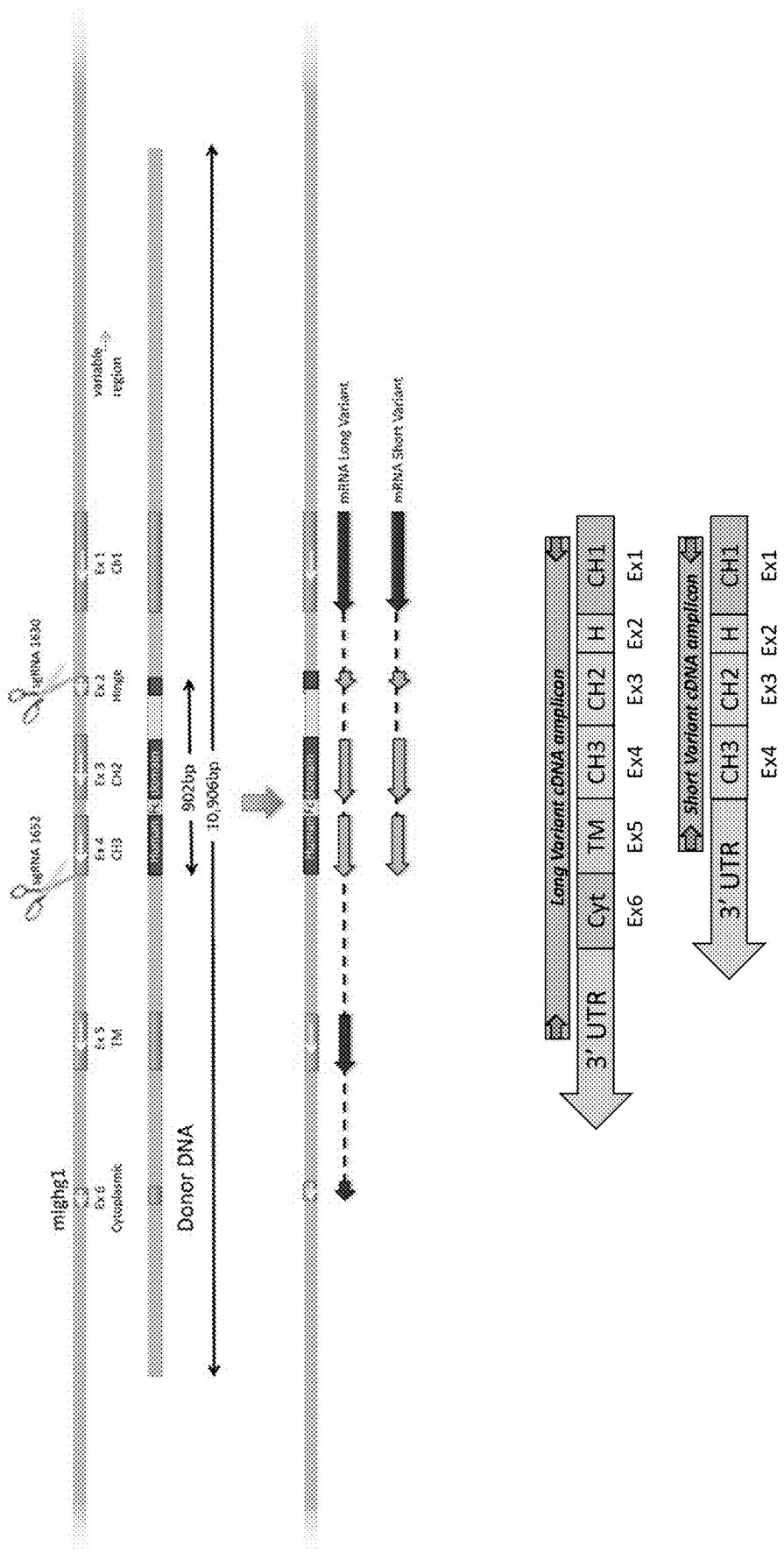
FIG. 2 shows the IgG1 domains in the mouse genome, the donor DNA encoding human IgG1, and the mouse genome after removal of the mouse hinge and Fc region (mC$_{H2}$ and mC$_{H3}$) and insertion of the human hinge and Fc region (hC$_{H2}$ and hC$_{H3}$). Transmembrane, TM. Predicted mRNAs from the region were verified by RT-PCR; note both isoforms were found and their correct splicing and sequence confirmed. Mouse sequence is shown in blue, human in green.

Example 1. Production of Mice Expressing Chimeric Mouse/Human IgG1 and Human FcRn To produce mice expressing a chimeric mouse/human IgG1 and expressing human neonatal Fc receptor (FcRn), encoded by Fcgrt, Fc receptor, IgG, alpha chain transporter, the B6.Cg-Fcgrt$^{tm1Dcr}$ Tg(FCGRT)32Dcr/DcrJ (also referred to as Tg32) mouse strain as modified using CRISPR/Cas9 gene editing technology. Single guide RNAs (gRNAs) were designed to bind to the genomic region flanking the mouse immunoglobulin 1 (mIgG1) Fc and hinge locus. The donor DNA, carrying a human hinge and Fc sequence, included 2-3 kilobase (kb) homology arms flanking the mouse hinge and Fc sequence. Cas9 mRNA, the gRNAs (SEQ ID NO: 4 and SEQ ID NO: 5), and the donor DNA were injected into Tg32 mouse embryos followed by CRISPR-mediated homologous recombination to produce chimeric IgG1 (FIGS. 1 and 2).

Eighty-seven (87) live born mice were analyzed by polymerase chain reaction (PCR) for correct integration of the donor DNA (with human IgG1 Fc and hinge sequence). Three founder animals were identified, of which two transmitted the humanized Fc and hinge domain (B6.Cg-Fcgrt$^{tm1Dcr}$ Ighg1$^{em2(IGHG1)Mvw}$ Tg(FCGRT)32Dcr/Mvw; also referred to as Tg32-hFc, JAX Stock #029686), one of which, referred to herein asTg32-hFc, was used for further studies.

Example 2. Modeling Human FcRn-Mediated Antibody Recycling

To assess whether the chimeric IgG1 cDNA was being synthesized in the Tg32-hFc mouse model provided herein, spleens were taken from mice of the Tg32-hFc strain and from mice of the Tg32 strain and subjected to RT-PCR. Chimeric IgG1 cDNA was detected in the Tg32-hFc mice, and endogenous mouse IgG1 cDNA was detected in the Tg32 mice. All results were verified by sequencing (data not shown).

Figure 3:
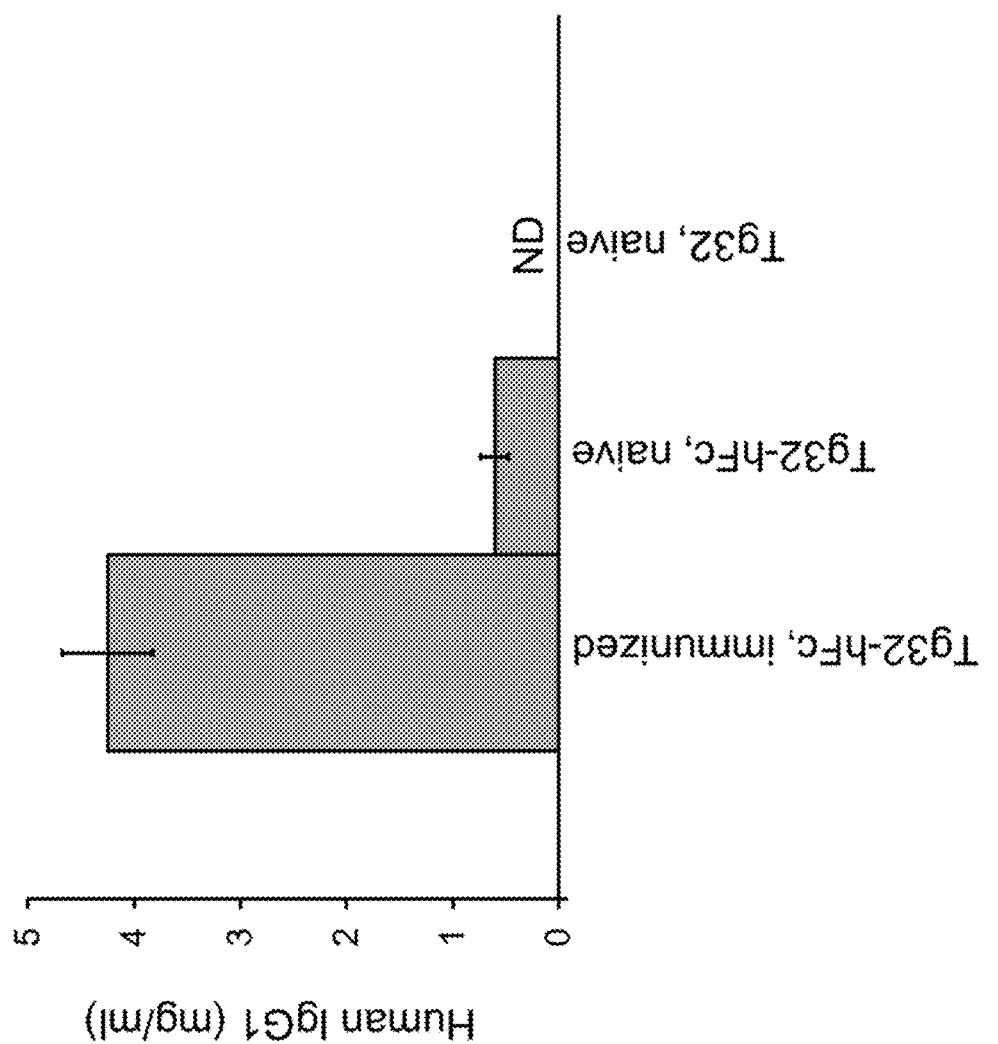
FIG. 3 shows the serum level of total human IgG1 Fc in milligrams per milliliter (mg/mL). "Tg32-hFc" is a mouse strain of the present disclosure expressing human FcRn and chimeric mouse/human IgG1 (see FIG. 1). "Tg32" is a mouse strain expressing human FcRn and endogenous mouse IgG1. Tg32-hFc, Immunized values are from a 1:160,000 serum dilution; Tg32-hFc, Non-Immunized values are from a 1:40,000 serum dilution; and Tg32, Non-Immunized values are from a 1:20,000 serum dilution. Immunized means that the mice are injected with 2,4-Dinitrophenyl hapten conjugated to keyhole limpet hemocyanin (DNP-KLH) and non-immunized means that the mice are not injected with DNP-KLH. The values plotted are average±SEM. See also Table 1 and FIG. 3 of Low, B. E., et al. (2020).
Figure 4:
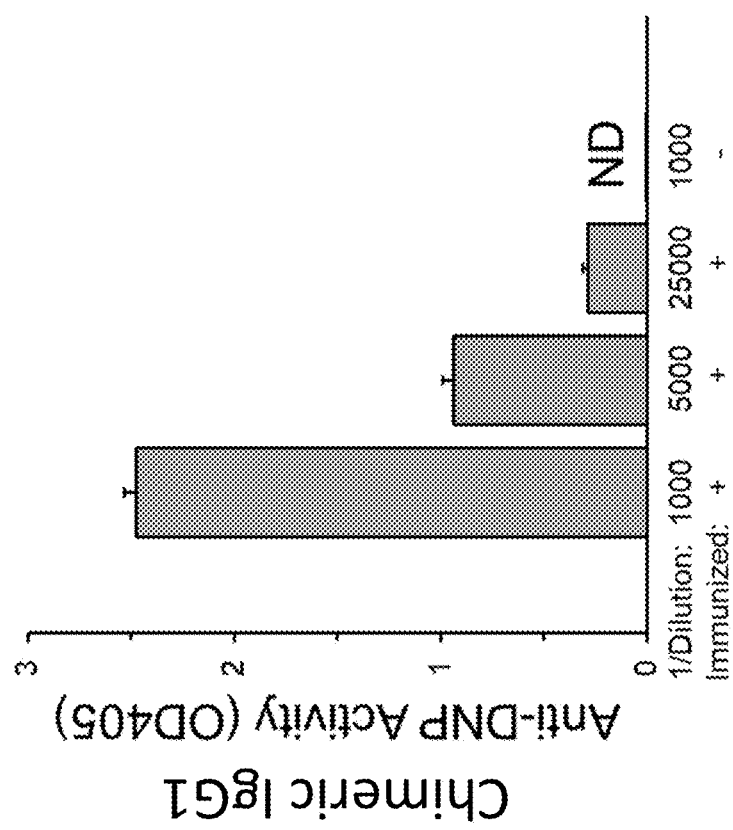
FIG. 4 shows the chimeric IgG1 anti-2,4-Dinitrophenyl (DNP) activity resulting following immunization of Tg32-hFc with DNP-KLH. Serum collected 2 weeks after the second immunization was diluted 1:1000, 1:5000, or 1:25000 then added to ELISA plates coated with DNPbovine albumin, detected using mouse anti-human IgG1 Fc-alkaline phosphatase. Following incubation with substrate, OD405 was read. Unimmunized (naïve) Tg32-hFc serum showed no anti-DNP activity when diluted 1:1000. The values plotted are average±SEM. See also FIG. 2d of Low, B. E., et al. (2020).

Mice of both the Tg32-hFc strain and the Tg32 strain express human FcRn at physiologically-relevant human levels from the endogenous human FCGRT promoter. For mice of the Tg32-hFc strain to mimic competition for human FcRn-mediated IgG1 recycling, serum chimeric IgG1 levels should also be physiologically relevant for humans. Serum chimeric IgG1 levels were measured in Tg32-hFc mice either immunized or non-immunized with 2,4-Dinitrophenyl hapten conjugated to keyhole limpet hemocyanin (DNP-KLH). Surprisingly, the serum IgG1 level was ~4.8 mg/mL in non-immunized mice and rose to ~29 mg/mL following immunization (FIG. 3). Serum IgG1 levels in humans are typically 4.9-11 mg/mL (see, e.g., Van Kessel, et al., Clin. Ex. Immunol., 1999, 118(1): 102-107), thus the serum IgG1 levels of immunized Tg32-hFc mice are approach physiologically-relevant levels for humans, mimicking competition conditions for human FcRn-mediated IgG1 recycling.

Human or humanized monoclonal IgG1 antibodies in humans compete with endogenous serum IgG1 for hFcRn-mediated antibody recycling. The serum half-life of IgG1 was measured in Tg32-hFc mice to ensure that competition for hFcRn-mediated antibody recycling was occurring (see FIG. 3 of Low, B. E., et al. 2020). Tg32-hFc mice expressing chimeric IgG1 were injected with the humanized monoclonal IgG1 antibody trastuzumab (HERCEPTIN®) to examine competition for human FcRn recycling of IgG1 antibodies. Additionally, when injected with humanized mAbs, for example trastuzumab, this yielded a half-life of 8.8+/−0.6 days in naïve Tg32 mice, while transgenic expression of Fc humanized IgG1 in Tg32-hFc mice reduced half-life of trastuzumab to 7.4+/−0.2 days (naïve, p=0.06) and 6.5+/−0.3 days (immunized, p=0.01). "Naïve" refers to mice not previously contacted with an antigen (e.g., DNP-KLH), and "immunized" refers to mice previously contacted with an antigen (e.g., DNP-KLH). The serum half-life of trastuzumab in humans is 2-12 days, depending on dosage (see, e.g., "Trastuzumab", DrugBank, drugbank.ca/drugs/DB00072). The decrease in serum half-life of the humanized trastuzumab antibody in Tg32-hFc mice expressing chimeric IgG1 suggests that there is increased competition for human FcRn-mediated recycling of IgG1, and that these mice closely recapitulate human FcRn-mediated antibody recycling.

SEQUENCES

Mouse genomic region with chimeric human IgG1 (human region underlined-replaces mouse hinge, CH2 and CH3)

(SEQ ID NO: 1)
AACAAGAACAGGGGAAATCCTAGGGCTGACATTGCCAGTGGAAACATACAGGCTGGAGCTCTTT

AGTCAGGAGCTCCAGCTGTGATCTAGACATCAGGCAGGAAGATCAAATCTGTCCCAACAATACA

GGGGACAGAGGCTCAACCTAGAGTGTGAGCATCAGGGGCTGTGCAGGAGATTTCAGAGCTCAGG

TGCAGCAGAGACTAGCATGGCCCTGGGGATAAAGGGAAGGATCCAAGGGACAAGGGGATAATCC

TGGGGAGGTAAGGGCCAGCTTCGTGACAGAAGGTGGTGGTGTCCAACTTCAAGAGCCCTGTGCT

ACAATTTAAAAAAAAAAAAAAAGGAAAGGGACTTCTCTGTGTTTGGCAACACAAGTGCGATGCA

CAGGCAGGAAGATCAAATCTGTCCCAACAATACAGGGGACAGAGGGTCAACCTACAAAAGGAAA

GAACCTGGGCAGTGTGAAGACAACACTGTAGAAGCCAAGGCTGAGTTCACTGAGCTCTCGTTA

GTGAGACTACACAGCAAGGAGGTGGCGGGCACTGAGCAGTGAGGCCCCGGGAAGTGGGGGTGAT

GGTGGTGACGGTGGTAACTGTTAAGAACTGGGGGAAAGAATTGTGGAGAACCAAGCTAAATAGT

TATGTCAAACCACATGTTTAGGAGCCTGGGTTGACTTCATAGGGAGTAGGCATGGAGGCTAATC

TAGAGGTTTGTGTATAGGCAAGAAGTGAATCCTGACCCAAGAATAGAGAGTGCTAAACGGACTT

AGTTCAAAGACAACTGAAAAAGACAATGCCTGCAAAACAAAGCTAAGGCCAGAGCTCTTGGACT

ATGAAGAGTTCAGGGAACCTAAGAACAGGGACCATCTGTGTACAGGCCAAGGCCGGTAGAAGCA

GCCTAGGAAGTGTCAAGAGCCAACGTGGCTGGGTGGGCAAAGACAGGAAGGGACTGTTAGGCTG

CAGGGATGTGCCGACTTCAATGTGCTTCAGTATTGTCCAGATTGTGTGCAGCCATATGGCCCAG

GTATAAGAGGTTTAACAGTGGAACACAGATGCCCACATCAGACAGCTGGGGGGGGGGGTGAAC

ACAGATACCCATACTGGAAAGCAGGTGGGGCATTTTCCTAGGAACGGGACTGGGCTCAATGGCC

TCAGGTCTCATCTGGTCTGGTGATCCTGACATTGATAGGCCCAAATGTTGGATATCACCTACTC

CATGTAGAGAGTCGGGGACATGGGAAGGGTGCAAAAGAGCGGCCTTCTAGAAGGTTTGGTCCTG

TCCTGTCCTGTCTGACAGTGTAATCACATATACTTTTTCTTGTAGCCAAAACGACACCCCCATC

TGTCTATCCACTGGCCCCTGGATCTGCTGCCCAAACTAACTCCATGGTGACCCTGGGATGCCTG

GTCAAGGGCTATTTCCCTGAGCCAGTGACAGTGACCTGGAACTCTGGATCCCTGTCCAGCGGTG

TGCACACCTTCCCAGCTGTCCTGCAGTCTGACCTCTACACTCTGAGCAGCTCAGTGACTGTCCC

CTCCAGCACCTGGCCCAGCCAGACCGTCACCTGCAACGTTGCCCACCCGGCCAGCAGCACCAAG

GTGGACAAGAAAATTGGTGAGAGGACGTATAGGGAGGAGGGGTTCACTAGAGGTGAGGCTCAAG

CCATTAGCCTGCCTAAACCAACCAGGCTGGACAGCCATCACCAGGAAATGGATCTCAGCCCAGA

AGATCGAAAGTTGTTCTTCTCCCTTCTGGAGATTTCTATGTCCTTTACACTCATTGGTTAATAT

CCTGGGTTGGATTCCCACACATCTTGACAAACAGAGACAATTGAGTATCACCAGCCAAAAGTCA

TACCCAAAAACAGCCTGGCATGACCTCACACCAGACTCAAACTTACCCTACCTTTATCCTGGTG

GCTTCTCATCTCCAGACCCCAGTAACACATAGCTTTCTCTCCACAGT<u>GCCCAAATCTTGTGACA</u>

<u>AAACTCACACATGCCCACCGTGCCCAGGTAAGCCAGCCCAGGCCTCGCCCTCCAGCTCAAGGCG</u>

<u>GGACAGGTGCCCTAGAGTAGCCTGCATCCAGGGACAGGCCCCAGCCGGGTGCTGACACGTCCAC</u>

<u>CTCCATCTCTTCCTCAGCACCTGAACTCCTGGGGGGACCGTCAGTCTTCCTCTTCCCCCCAAAA</u>

<u>CCCAAGGACACCCTCATGATCTCCCGGACCCCTGAGGTCACATGCGTGGTGGTGGACGTGAGCC</u>

<u>ACGAAGACCCTGAGGTCAAGTTCAACTGGTACGTGGACGGCGTGGAGGTGCATAATGCCAAGAC</u>

<u>AAAGCCGCGGGAGGAGCAGTACAACAGCACGTACCGTGTGGTCAGCGTCCTCACCGTCCTGCAC</u>

<u>CAGGACTGGCTGAATGGCAAGGAGTACAAGTGCAAGGTCTCCAACAAAGCCCTCCCAGCCCCCA</u>

<u>TCGAGAAAACCATCTCCAAAGCCAAAGGTGGGACCCGTGGGGTGCGAGGGCCACATGGACAGAG</u>

<u>GCCGGCTCGGCCCACCCTCTGCCCTGAGAGTGACCGCTGTACCAACCTCTGTCCCTACAGGGCA</u>

-continued

```
GCCCCGAGAACCACAGGTGTACACCCTGCCCCATCCCGGGATGAGCTGACCAAGAACCAGGTC

AGCCTGACCTGCCTGGTCAAAGGCTTCTATCCCAGCGACATCGCCGTGGAGTGGGAGAGCAATG

GGCAGCCGGAGAACAACTACAAGACCACGCCTCCCGTGCTGGACTCCGACGGCTCCTTCTTCCT

CTACAGCAAGCTCACCGTGGACAAGAGCAGGTGGCAGCAGGGGAACGTCTTCTCATGCTCCGTG

ATGCATGAGGCTCTGCACAACCACTACACACAGAAGAGCCTCTCCCTGTCTCCTGGTAAATGAT

CCCAGTGTCCTTGGAGCCCTCTGGTCCTACAGGACTCTGACACCTACCTCCACCCCTCCCTGTG

TAAATAAAGCACCCAGCACTGCCTTGGGACCCTGCAATAATGTCCTGGTGATTTCTGAGATGTA

GAGTCTAGCTAGGTCATGGAATGAGGGGTCTCCATGGTTTGAGGCCTGAGTTGTGACTAAGGAA

AAACCCATAGGCCTACACTGCCACACCCAGCACTTTTGAATTTGCCTGACATGAAAAGAATTTA

CCTCTCCCTGGAAAGTGGAGCCTTATCCCTAGGCAGTTCCCTTACCAGACCTTCCTCTAGCTTG

CACTTTGTTCTGGGCACAGAATGTGTCTAACCCCCCAAAGCAAGGAAGACACAACCTCTACCTC

CCTCACTCTGTCCTTACCCCTTTTCCTGGCTAAGCATCTCACTGAGTGCGCTGAATAGATGCAT

GTGGCCACAGTCTTGCAGACAGACCCTTGCCATCTCTCCACTCAGCTTTCCAGAGGCTAAGTCT

AGCCCGTATGGTGATAATGCAGGGAGCTCTATGCTATCTCAGTGCTATCAGACTCCCAAGTGGA

GGATGAACATGGACCCATTAAAACCAACCTGCGCAGCAACACCCTGCCAATAAGGCCCGTATGT

GAAAATGTGCACACATCTACACATGCACAGGCACACACACACACACATGCATGGGCACACACAC

ATACAGAGAGAGAGAATCACAGAAACTCCCATGAGCATCCTATACAGTACTCAAAGATAAAAG

GTACCAGGTCTACCCACATGATCATCCTCGGCATTTACAAGTGGGCCAACTGATACAGATAAAA

CTTTTCTATGCCAAGGACGCCAACATATACACAAGTCCGCTCATGACAAATCTGTCCCTGAACC

TCAGACTGGCGCCCGTGACTCATACAGTGGACACTCCTCCAAAGCTGTATAGCTTCCTTTACTT

CCCTGTGTGTACTTTCTCTGAAGTACACTCATCACACAGAAGAGGCCCTGTGATTACTCTGGCC

CTCTGTTCTTGGTCATCAGAGAATAGACAGAAGATCAGGCAAACTACACAGACACTTCCCACAA

TCATCACAGGCCCTGACTCTGCTCTCCAGTCTCAAAACTGAAGGCTGGAGCACACAGAATAAGC

TCCTGCACAGGCCAGGCCAGTATCGGGTCCAGTGTGTCTGACTGAGCCCAGGGACAAAATGGCA

GCACTTTGGGGAACTGAGGTTTCTGGTCCAAGAAGGAGAGATGGAGGCCCAGGGAGGGTCTGCT

GACCCAGCCCAGCCCAGCTGCAGCTTTCTCCTGGGCCTCCATACAGCCTCCTGCCACAC

AGGGAATGGCCCTAGCCCCACCTTATTGGGACAAACACTGACCGCCCTCTCTGTCCAGGGCTGC

AACTGGACGAGACCTGTGCTGAGGCCCAGGACGGGGAGCTGGACGGGCTCTGGACGACCATCAC

CATCTTCATCAGCCTCTTCCTGCTCAGTGTGTGCTACAGCGCTGCTGTCACACTCTTCAAGGTC

AGCCATACTGTCCCCACAGTGTCTACAATGTCCTCATACTCTTCCCCATACTGTCCCTGTGGTG

ACCTATACCCCACACTGTCCCATGCTAATGACCACAGTCTTACATGCTATGTAATGCTGTCTAC

CCTTCTGTATGCACAGTCTCACAATGTCCCATGCAGTCTCCACGATGCTCCATACTGTCCCCAT

TCCAACCCATGCTGCCCTTGTTCCCCGCTATGCTGTCCCATGCTATTGTCTGTATTTTCATGC

TCTTTTCACACTGTCCCTAGTGTCACATTCTGCCCATGTTGTCCACCACATTGTCCCCACTCTG

TACACAGCCTCACACTGTACCCTGCTACCCGATAATGTTCCCTGTTGTCCCCAACTCTCTCCCT

GCACCATTTGTCAACTGTCCCCTGAATTCCCATGTTGTTCCCACACTGTTAGTGTGTAATGTGC

TCTGTCCCA
```

Human IgG1 Fc Hinge (SEQ ID NO: 2)
PKSCDKTHTCP

Human IgG1 Fc Heavy Chain (SEQ ID NO: 3)
PCPAPELLGGPSVFLFPPKPKDTLMISRTPEVTCVVVDVSHEDPEVKEN
WYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVF
SCSVMHEALHNHYTQKSLSLSPGK gRNA-1

(SEQ ID NO: 4)
GCACAATCCCTGGGCACTGTGG gRNA-2

(SEQ ID NO: 5)
GAGCCTCTCCCACTCTCCTGG chimeric IgG1 heavy chain, long variant, including human Fc hCH2, human hCH3, mouse CH1 (human region underlined-replaces mouse hinge, CH2 and CH3)

(SEQ ID NO: 6)
KTTPPSVYPLAPGSAAQTNSMVTLGCLVKGYFPEPVTVTWNSGSLSSGV
HTFPAVLQSDLYTLSSSVTVPSSTWPSQTVTCNVAHPASSTKVDKKI<u>VP
KSCDKTHTCPPCPAPELLGGPSVFLFPPKPKDTLMISRTPEVTCVVVDV
SHEDPEVKENWYVDGVEVHNAKTKPREEQYNSTYRVVSVLIVLHQDWLN
GKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVD
KSRWQQGNVFSCSVMHEALHNHYTQKSLSLSPGLQLDETCAEAQDGELD
GLWTTITIFISLFLLSVCYSAAVTLFKVKWIFSSVVELKQTLVPEYKNM
IGQAP</u> chimeric IgG1 heavy chain, short variant, including human Fc hCH2, human Fc hCH3, mouse CH1, (human regions underlined-replaces mouse hinge, CH2, and CH3)

(SEQ ID NO: 7)
KTTPPSVYPLAPGSAAQTNSMVTLGCLVKGYFPEPVTVTWNSGSLSSGV
HTFPAVLQSDLYTLSSSVTVPSSTWPSQTVTCNVAHPASSTKVDKKI<u>VP
KSCDKTHTCPPCPAPELLGGPSVFLFPPKPKDTLMISRTPEVTCVVVDV
SHEDPEVKFNWYVDGVEVHNAKTKPREEQYNSTYRVVSVLIVLHQDWLN
GKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVD
KSRWQQGNVFSCSVMHEALHNHYTQKSLSLSPGK</u>

What is claimed is:

1. A mouse comprising:
a nucleic acid encoding human neonatal Fc receptor (FCRN); and
a nucleic acid, or a set of nucleic acids, encoding a chimeric immunoglobulin that comprises a mouse light chain variable region, a mouse light chain constant region, a mouse heavy chain variable region, and a chimeric heavy chain constant region comprising the amino acid sequence of SEQ ID NO: 6 or SEQ ID NO: 7,
wherein the mouse comprises a null mutation in endogenous FcRn.

2. The mouse of claim 1, wherein cells of the mouse express the human FCRN and the chimeric immunoglobulin.

3. The mouse of claim 1, wherein the immunoglobulin comprises a human hinge sequence.

4. The mouse of claim 3, wherein the human hinge sequence comprises the amino acid sequence of SEQ ID NO: 2.

5. The mouse of claim 1, wherein the nucleic acid encoding the immunoglobulin comprises a sequence that has at least 90% identity to the sequence of SEQ ID NO: 1.

* * * * *